(12) United States Patent
Yang et al.

(10) Patent No.: US 6,689,870 B1
(45) Date of Patent: Feb. 10, 2004

(54) PROTEIN MACROMOLECULAR DYES

(75) Inventors: Jinzong Yang, Dalian (CN); Shufen Zhang, Dalian (CN)

(73) Assignees: China Petro-Chemical Corporation, Beijing (CN); Dalian University of Technology, Dalian (CN)

( * ) Notice: Subject to any disclaimer, the term of this patent is extended or adjusted under 35 U.S.C. 154(b) by 0 days.

(21) Appl. No.: 09/116,743

(22) Filed: Jul. 16, 1998

(51) Int. Cl.$^7$ .................................................. C08H 1/00
(52) U.S. Cl. ........................ 530/402; 530/350; 530/354; 530/405; 427/323; 28/167; 252/8.57; 252/8.6; 252/8.7; 534/558
(58) Field of Search ........................... 28/167; 252/8.57, 252/8.6, 8.7; 427/323; 534/558; 530/354, 350, 402

(56) References Cited

U.S. PATENT DOCUMENTS

| | | | |
|---|---|---|---|
| 3,758,470 A | * 9/1973 | Ackermann | 544/189 |
| 4,477,635 A | 10/1984 | Mitra | 525/437 |
| 4,546,161 A | 10/1985 | Harvey et al. | 527/312 |
| 5,192,332 A | * 3/1993 | Lang et al. | 8/405 |

FOREIGN PATENT DOCUMENTS

EP    0 205 290    12/1986

OTHER PUBLICATIONS

Stanislaw et al., *Chemical Abstracts*, vol. 93, 1980, Chem Abst. No. 27725x.*
Chekalin et al., *Chemical Abstracts*, vol. 70, 1969, Chem Abst. No. 58895g.*
Simov et al., *Chemical Abstracts*, vol. 78, 1973, Chem Abst. No. 160795b.*
Wolf et al., *Chemical Abstracts*, vol. 69, 1968, Chem Abst. No. 20362x.*
Alsberg, Rev. Prog. Color. Relat. Top. 12, 66–72, 1982.*
Collishaw, Colourage 48(11), 13–20, 2001.*
Achwall, Colourage Annual 93–95, 1996.*
Ashutosh, Tinctoria 77(12), 401–4, 1980.*
Anon, Colour. Annu. 93–8, 1986.*
Wu, Zuwang, Review of Progress in Coloration and Related Topics 28, 32–38, 1998.*
Nalankilli, G., Colourage 40(7), 29–32, 1993.*
Gulrajani, M. L., Review of Progress in Coloration and Related Topics 23, 51–6, 1993.*
Shore, John, J. Soc. Dyers Colour. 84(8), 413–22, 1968.*

* cited by examiner

*Primary Examiner*—Christopher S. F. Low
*Assistant Examiner*—David Lukton
(74) *Attorney, Agent, or Firm*—Alston & Bird LLP

(57) ABSTRACT

Protein macromolecular dyes, $A(B)_b$, are disclosed, wherein A are protein macromolecules including natural protein macromolecules and modified natural protein macromolecules such as casein, gelatin and fur-protein; B are dyes including azo dyes, azo metal complex dyes and anthraquinone dyes which can react with the amino groups of the natural and modified protein macromolecules; b are integers between 1~2500. The protein macromolecular dyes have excellent properties of crosslinking ability, better dyeing fastness, fixation ration than conventional dyes and the function of normal macromolecules such as compatibility, abilities of filling and forming membranes. They may be used in dyeing protein materials such as leather, wool and silk.

10 Claims, No Drawings

PROTEIN MACROMOLECULAR DYES

This invention relates to protein macromolecular dyes, especially to the protein macromolecular dyes which are prepared by reacting protein macromolecules with the reactive dyes.

There were descriptions related to polymeric dyes in the prior art. In European patent publication No. 0 205 290 (1986), colored polymer was prepared by the copolymerization of the azo dyes containing unsaturated olefin. And U.S. Pat. No. 4,477,635 described the preparation of polymeric triarylmethane dye by polycondensation. The defect of preparing polymeric dye by copolymerization or polycondensation was that dyes and intermediates in copolymerization and polycondensation should not contain the inhibited groups such as nitro and amino groups. But these inhibited groups were necessary auxochromo groups for bright dyes. Therefore, the conversion of the dyes and the content of the parent dyes in the polymeric dyes were low when the conventional dyes were used in the polymerization for preparing polymeric dyes.

In U.S. Pat. No. 4,546,161 (1985) an affinity chromatography carrier for protein separation was described. Polymer and copolymer of agarose, dextrose, dextran and acrylamide was used as the support matrix of the carrier bearing mono- or dichloro triazine dyes which were added by chemical reaction. The combination amount of the dye combined onto the macromolecule was lower than 10% in the carrier.

As the content of the parent dyes on the support matrix in the prior macromolecule is low, the present invention suggests protein macromolecular dyes with high content of the parent dyes. It is synthesized by the reaction of the amino groups of protein macromolecules used as polymeric support matrix with parent dyes.

So far, there is no report about protein macromolecular dyes in publications.

The object of the present invention is to provide protein macromolecular dyes synthesized by the reaction of protein macromolecules with dyes, and to overcome the low binding amount of the parent dyes in macromolecular support matrix of prior macromolecular dyes. This kind of protein macromolecular dyes has good properties such as color brightness, coloring ability, fastness, anti-mobility, compatibility and environmental safety in dyeing protein materials such as leather, wool and silk.

The present invention provides protein macromolecular dyes having the formula:

wherein A are protein macromolecules, B are dyes which can react with the amino groups of the protein macromolecules, b are integers between 1~2500.

The present invention provides protein macromolecular dyes wherein dyes B are azo dyes, which can react with the amino groups of the protein macromolecules A.

The present invention provides protein macromolecular dyes wherein dyes B are azo metal complex dyes, which can react with the amino groups of the protein macromolecules A.

The present invention provides protein macromolecular dyes wherein dyes B are anthraquinone dyes, which can react with the amino groups of the protein macromolecules A.

The present invention provides protein macromolecular dyes wherein the protein macromolecules A are natural protein macromolecules with 1000~450000 molecular weight.

The present invention provides protein macromolecular dyes wherein the protein macromolecules A which can react with the azo dyes are natural protein macromolecules with 1000~450000 molecular weight.

The present invention provides protein macromolecular dyes wherein the protein macromolecules A which can react with the azo metal complex dyes are natural protein macromolecules with 1000~450000 molecular weight.

The present invention provides protein macromolecular dyes wherein the protein macromolecules A which can react with the anthraquinone dyes are natural protein macromolecules with 1000~450000 molecular weight.

The present invention provides protein macromolecular dyes wherein the natural protein macromolecules A which can react with the dye B is casein with 1000~450000 molecular weight.

The present invention provides protein macromolecular dyes wherein the natural protein macromolecule A which can react with the dye B is gelatin with 1000~450000 molecular weight.

The present invention provides protein macromolecular dyes wherein the natural protein macromolecule A which can react with the dye B is fur-protein with 1000~450000 molecular weight.

The present invention provides protein macromolecular dyes wherein the natural protein macromolecule A which can react with the azo dye B is casein with 1000~450000 molecular weight.

The present invention provides protein macromolecular dyes wherein the natural protein macromolecule A which can react with the azo dye B is gelatin with 1000~450000 molecular weight.

The present invention provides protein macromolecular dyes wherein the natural protein macromolecule A which can react with the azo dye B is fur-protein with 1000~450000 molecular weight.

The present invention provides protein macromolecular dyes wherein the natural protein macromolecule A which can react with the azo metal complex dye B is casein with 1000~450000 molecular weight.

The present invention provides protein macromolecular dyes wherein the natural protein macromolecule A which can react with the azo metal complex dye B is gelatin with 1000~450000 molecular weight.

The present invention provides protein macromolecular dyes wherein the natural protein macromolecule A which can react with the azo metal complex dye B is fur-protein with 1000~450000 molecular weight.

The present invention provides protein macromolecular dyes wherein the natural protein macromolecule A which can react with the anthraquinone dye B is casein with 1000~450000 molecular weight.

The present invention provides protein macromolecular dyes wherein the natural protein macromolecule A which can react with the anthraquinone dye B is gelatin with 1000~450000 molecular weight.

The present invention provides protein macromolecular dyes wherein the natural protein macromolecule A which can react with the anthraquinone dye B is fur-protein with 1000~450000 molecular weight.

The present invention provides protein macromolecular dyes wherein the protein macromolecule A for preparing protein macromolecular dyes are expressed as follows:

wherein A' are the modified protein macromolecules derived from the protein macromolecules A of which 0.1~95% amino groups are substituted by the dye, d are integers between 1~2400, D are single or mixed groups as follows:

(1)

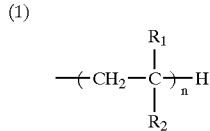

wherein $R_1$ is —H or —$CH_3$; n are integers between 1~1000; $R_2$ is —COOH, —$CONH_2$, —CN, —$COOCH_3$, —$COOC_2H_5$, —$COOC_3H_7$, —$COOC_4H_9$, —Cl, —CHO, —$COOC_2H_4OH$, or (2)

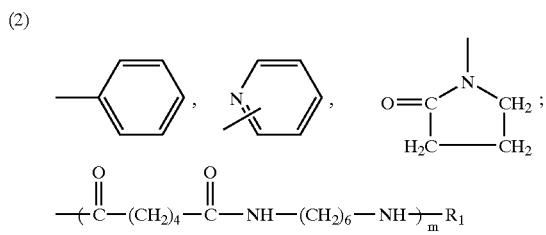

wherein m are integers between 1~200; $R_1$ is —H,

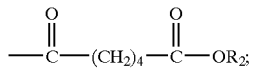

$R_2$ is —H, —$CH_3$, —$C_2H_5$;

(3)

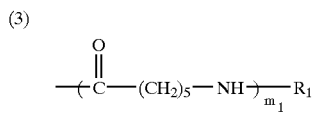

wherein $m_1$ are integers between 1~300; $R_1$ is —H, or

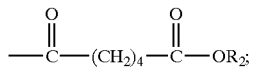

$R_2$ is H, —$CH_3$, or —$C_2H_5$.

The present invention provides protein macromolecular dyes wherein the protein macromolecules A which can react with the azo dyes are expressed as follows:

$$A'(D)_d \qquad (6)$$

wherein A' are the modified protein macromolecules derived from the protein macromolecules A of which 0.1~95% amino groups are substituted by the dye, d are integers between 1~2400, D are single or mixed groups as follows:

(1)

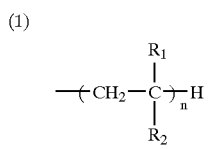

wherein $R_1$ is —H or —$CH_3$; n are integers between 1~1000; $R_2$ is —COOH, —$CONH_2$, —CN, —$COOCH_3$, —$COOC_2H_5$, —$COOC_3H_7$, —$COOC_4H_9$, —Cl, —CHO, —$COOC_2H_4OH$ or (2)

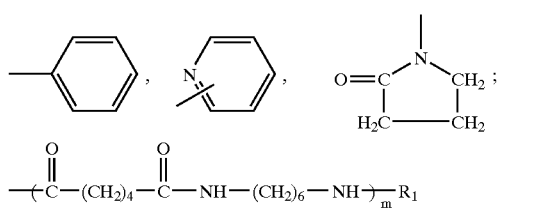

wherein m are integers between 1~200; $R_1$ is —H,

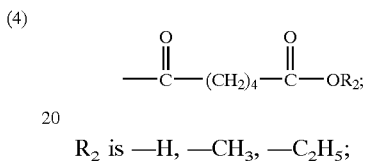

$R_2$ is —H, —$CH_3$, —$C_2H_5$;

(3)

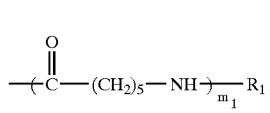

wherein $m_1$ are integers between 1~300; $R_1$ is —H,

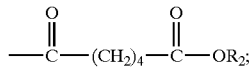

wherein $R_2$ is —H, —$CH_3$, —$C_2H_5$.

The present invention provides protein macromolecular dyes wherein the protein macromolecules A which can react with the azo metal complex dyes are expressed as follows:

$$A'(D)_d \qquad (10)$$

wherein A' are the modified protein macromolecules derived from the protein macromolecules A of which 0.1~95% amino groups are substituted by the dye, d are integers between 1~2400, D are single or mixed groups as follows:

(1)

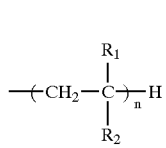

wherein $R_1$ is —H or —$CH_3$; n are integers between 1~1000; $R_2$ is —COOH, —$CONH_2$, —CN, —$COOCH_3$, —$COOC_2H_5$, —$COOC_3H_7$, —$COOC_4H_9$, —Cl, —CHO, —$COOC_2H_4OH$ or (2)

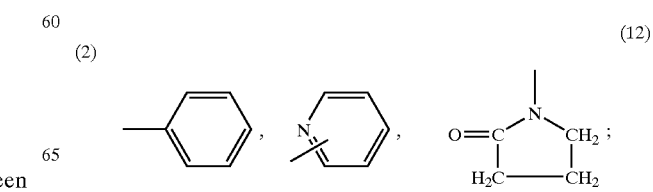

-continued

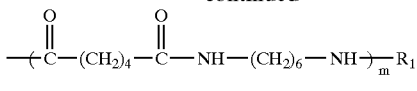

wherein m are integers between 1~200; $R_1$ is —H,

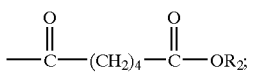

$R_2$ is —H, —CH$_3$, —C$_2$H$_5$;

(13)

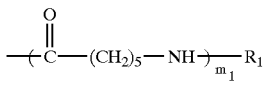

wherein $m_1$ are integers between 1~300; $R_1$ is —H, or

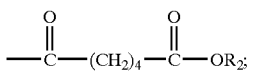

$R_2$ is —H, —CH$_3$, or —C$_2$H$_5$.

The present invention provides protein macromolecular dyes wherein the protein macromolecules A which can react with the anthraquinone dyes are expressed as follows:

A'(D)$_d$ (14)

wherein A' are the modified protein macromolecules derived from the protein macromolecules A of which 0.1~95% amino groups are substituted by the dye, d are integers between 1~2400, D are single or mixed groups as follows:

(1)

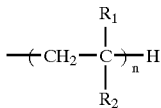

wherein $R_1$ is —H or —CH$_3$; n are integers between 1~1000; $R_2$ is —COOH, —CONH$_2$, —CN, —COOCH$_3$, —COOC$_2$H$_5$, —COOC$_3$H$_7$, —COOC$_4$H$_9$, —Cl, —CHO, —COOC$_2$H$_4$OH, or (2) (16)

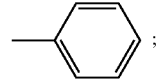

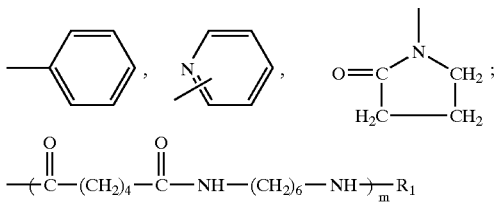

wherein m are integers between 1~200; $R_1$ is —H,

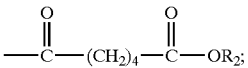

wherein $R_2$ is —H, —CH$_3$, or —C$_2$H$_5$;

(3) (17)

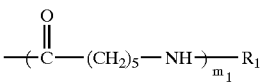

wherein $m_1$ are integers between 1~300; $R_1$ is —H, or

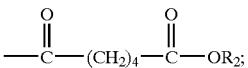

wherein $R_2$ is —H, —CH$_3$, or —C$_2$H$_5$.

The present invention provides protein macromolecular dyes wherein dye B which can react with the protein macromolecules including natural protein macromolecules such as casein, gelatin, fur-protein, and the modified protein macromolecules according to formula (2) and (6) is the azo dye which has the structure (18)

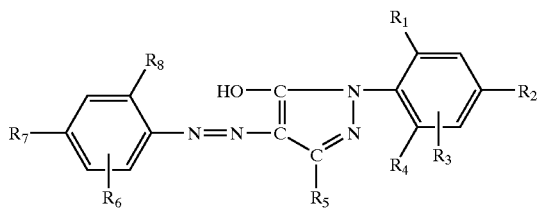

wherein $R_1$, $R_4$ and $R_8$ each represents —H, —Cl, —CH$_3$, —OCH$_3$, —OH, —COOX or —SO$_3$X respectively; $R_5$ is —H, —CH$_3$, —COOX, —SO$_3$X, or —SO$_2$NH$_2$,

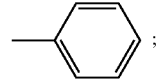

$R_2$, $R_3$, $R_6$ and $R_7$ each represents respectively —H, —Cl, —CH$_3$, —SO$_3$X, —COOX, —OCH$_3$, —NO$_2$, —SO$_2$NHR,

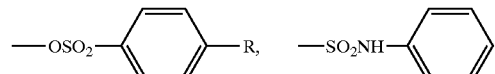

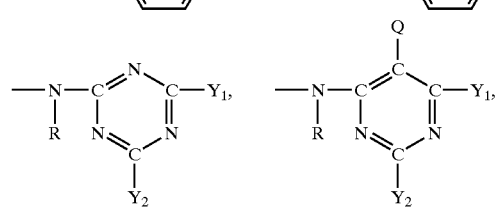

—SO$_2$CH$_2$CH$_2$Y$_3$, —SO$_2$NHCH$_2$CH$_2$Y$_3$,

—NHCOCY$_4$=CHY$_5$, or —NHCOCHY$_4$CH$_2$Y$_6$;

wherein Y$_1$ is —Cl, —F or —CH$_3$; Q is —Cl, —CH$_3$; Y$_2$ is —Cl, —F, —R, —OR, —NHCH$_2$SO$_3$X, —N(R)$_2$, —N(CH$_2$OH)$_2$, —SO$_2$R, —N(C$_2$H$_4$OH)$_2$,

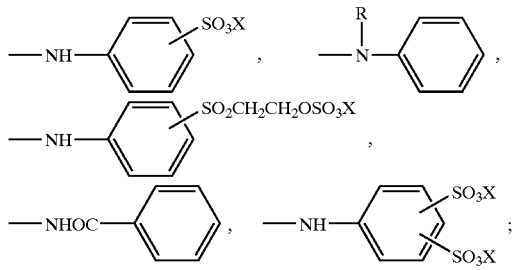

Y$_3$ is —Cl, —OSO$_3$X or —N(CH$_3$)CH$_2$CH$_2$SO$_3$X; Y$_4$ is —H or —Br; Y$_5$ is —H, —Cl or —Br; Y$_6$ is —Br or —OSO$_3$X; R is —H, —CH$_3$ or —C$_2$H$_5$; X is —H, —Na or —K.

The present invention provides protein macromolecular dyes wherein dye B which can react with the protein macromolecules including natural protein macromolecules such as casein, gelatin, fur-protein, and the modified protein macromolecules according to formula (2) and (6) is the azo dye which has the structure

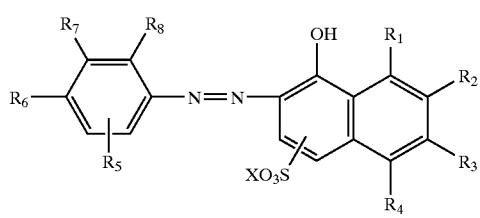

(19)

wherein R$_4$, R$_7$ and R$_8$ each represents —H, —CH$_3$, —OH, —OCH$_3$, —NO$_2$, —SO$_3$X, or —COOX respectively; R$_1$, R$_2$, R$_3$, R$_5$ and R$_6$ each represents respectively —H, —CH$_3$, —OR, —SO$_3$X, —Cl, —COOX, —CH$_2$SO$_3$X, —NO$_2$, —N(R)$_2$, —NHCONH$_2$, —NHCOCH$_3$,

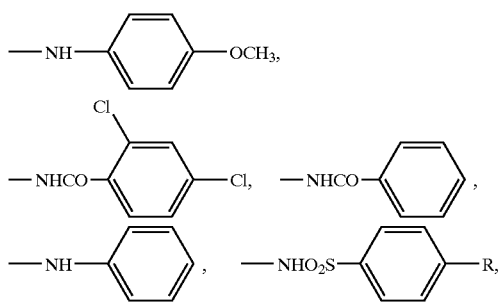

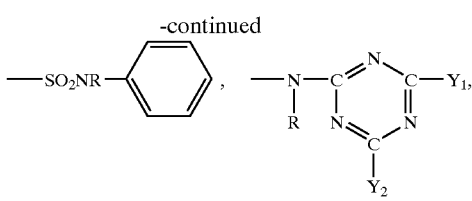

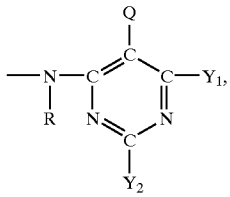

—SO$_2$CH$_2$CH$_2$Y$_3$,

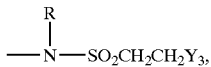

—SO$_2$NHCH$_2$CH$_2$Y$_3$, —NHCOCY$_4$=CHY$_5$, or —NHCOCHY$_4$CH$_2$Y$_6$; wherein Y$_1$ is —Cl, —F or —CH$_3$; Q is —Cl, —CH$_3$; Y$_2$ is —Cl, —F, —R, —OR, —NHCH$_2$SO$_3$X, —N(R)$_2$, —N(CH$_2$OH)$_2$, —SO$_2$R, —N(C$_2$H$_4$OH)$_2$,

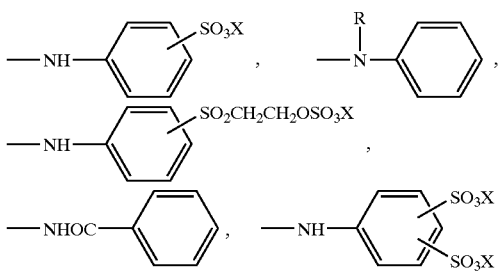

Y$_3$ is —Cl, —OSO$_3$X or —N(CH$_3$)CH$_2$CH$_2$SO$_3$X; Y$_4$ is —H or Br; Y$_5$ is —H, —Cl or —Br; Y$_6$ is —Br or —OSO$_3$X; R is —H, —CH$_3$ or —C$_2$H$_5$; X is —H, —Na or —K.

The present invention provides protein macromolecular dyes wherein dye B which can react with the protein macromolecules including natural protein macromolecules such as casein, gelatin, fur-protein, and the modified protein macromolecules according to formula (2) and (6) is the azo dye which has the structure

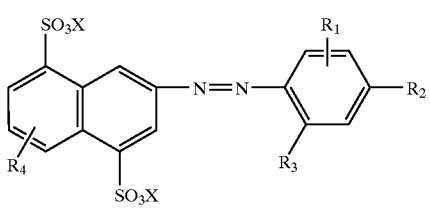

(20)

wherein R$_3$ is —H, —Cl, —CH$_3$, —OCH$_3$, —OH, —COOX, —SO$_3$X, —SO$_2$NH$_2$ or —NHCOCH$_3$; R$_1$, R$_2$ and R$_4$ each represents respectively —H,

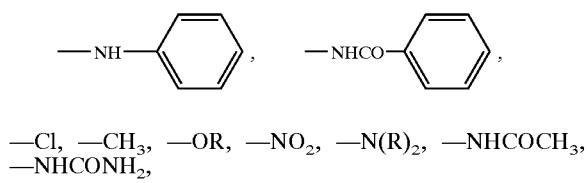

—Cl, —CH$_3$, —OR, —NO$_2$, —N(R)$_2$, —NHCOCH$_3$, —NHCONH$_2$,

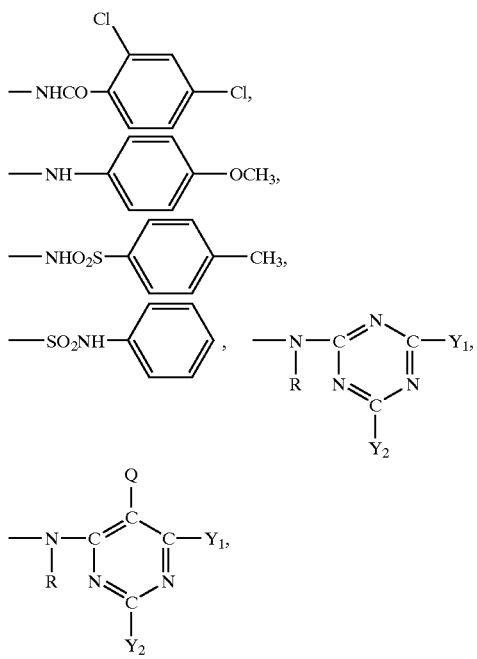

—SO$_2$CH$_2$CH$_2$Y$_3$,

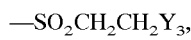

—SO$_2$NHCH$_2$CH$_2$Y$_3$, —NHCOCY$_4$=CHY$_5$, or —NHCOCHY$_4$CH$_2$Y$_6$; wherein Y$_1$ is —Cl, —F or —CH$_3$; Q is —Cl, —CH$_3$; Y$_2$ is —Cl, —F, —R, —OR, —NHCH$_2$SO$_3$X, —N(C$_2$H$_4$OH)$_2$, —N(R)$_2$, —N(CH$_2$OH)$_2$, —SO$_2$R,

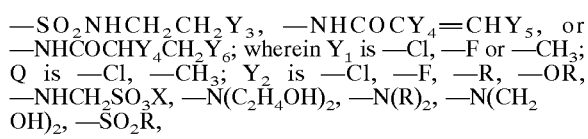
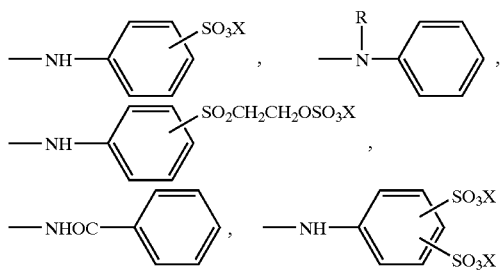

Y$_3$ is —Cl, —OSO$_3$X or —N(CH$_3$)CH$_2$CH$_2$SO$_3$X; Y$_4$ is —H or Br; Y$_5$ is —H, —Cl or —Br; Y$_6$ is —Br or —OSO$_3$X; R is —H, —CH$_3$ or —C$_2$H$_5$; X is —H, —Na or —K.

The present invention provides protein macromolecular dyes wherein dye B which can react with the protein macromolecules including natural protein macromolecules such as casein, gelatin, fur-protein, and the modified protein macromolecules according to formula (2) and (10) is the azo metal complex dye which has the structure

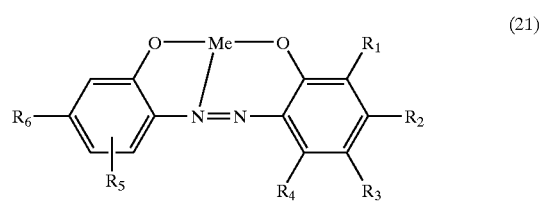

(21)

wherein Me is Cu, Co, Ni or Cr; R$_1$, R$_2$, R$_3$, R$_4$, R$_5$ and R$_6$ each represents respectively —H, —Cl, —CH$_3$, —OCH$_3$, —CH$_2$SO$_3$X, —NO$_2$, —SO$_3$X, —COOX, —NH$_2$, —N(CH$_3$)$_2$, —NHCOCH$_3$, —NHCONH$_2$,

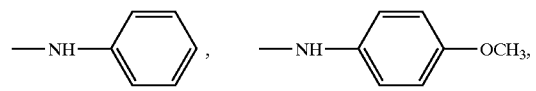
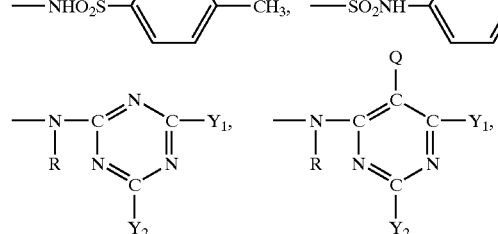

—SO$_2$CH$_2$CH$_2$Y$_3$,

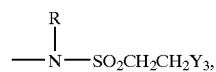

—SO$_2$NHCH$_2$CH$_2$Y$_3$, —NHCOCY$_4$=CHY$_5$, or —NHCOCHY$_4$CH$_2$Y$_6$; wherein Y$_1$ is —Cl, —F or —CH$_3$; Q is —Cl, —CH$_3$; Y$_2$ is —Cl, —F, —R, —OR, —N(R)$_2$, —NHCH$_2$SO$_3$X, —N(CH$_2$OH)$_2$, —SO$_2$R, —N(C$_2$H$_4$OH)$_2$,

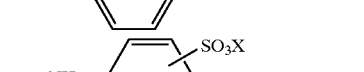
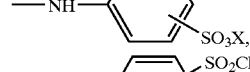

Y$_3$ is —Cl, —OSO$_3$X, —N(CH$_3$)CH$_2$CH$_2$SO$_3$X; Y$_4$ is —H or Br; Y$_5$ is —H, —Cl or —Br; Y$_6$ is —Br or —OSO$_3$X; R is —H, —CH$_3$ or —C$_2$H$_5$; X is —H, —Na or —K.

The present invention provides protein macromolecular dyes wherein dye B which can react with the protein macromolecules including natural protein macromolecules such as casein, gelatin, fur-protein, and the modified protein macromolecules according to formula (2) and (10) is the azo metal complex dye which has the structure

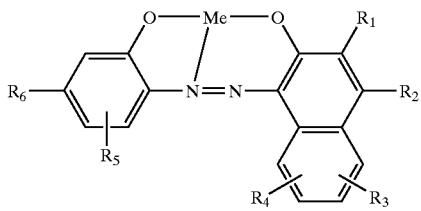
(22)

wherein Me is Cu, Co, Ni or Cr; $R_1$, $R_2$, $R_3$, $R_4$, $R_5$ and $R_6$ each represents respectively —H, —Cl, —$CH_3$, —$OCH_3$, —$SO_3X$, —COOX, —$CH_2SO_3X$, —$NH_2$, —$N(CH_3)_2$,

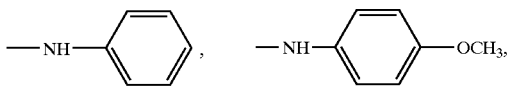

—$NHCOCH_3$, —$NHCONH_2$,

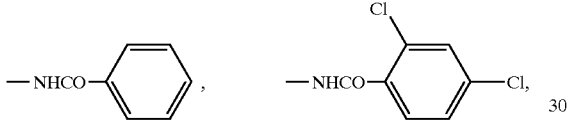

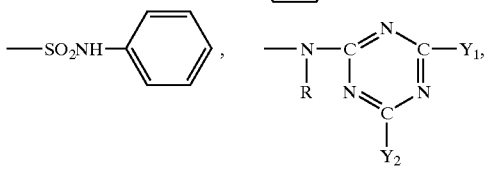

—$SO_2CH_2CH_2Y_3$, —$SO_2NHCH_2CH_2Y_3$,

—$NHCOCY_4$=$CHY_5$, or —$NHCOCHY_4CH_2Y_6$; wherein $Y_1$ is —Cl, —F or —$CH_3$; Q is —Cl, —$CH_3$; $Y_2$ is —Cl, —F, —R, —OR, —$NHCH_2SO_3X$,

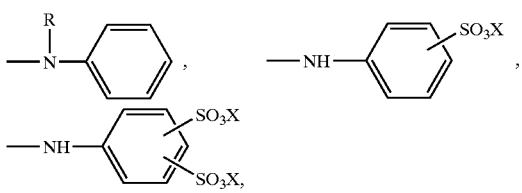

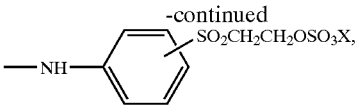

—$N(R)_2$, —$N(CH_2OH)_2$, —$N(C_2H_4OH)_2$, —$SO_2R$,

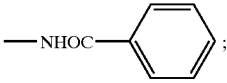

$Y_3$ is —Cl, —$OSO_3X$ or —$N(CH_3)CH_2CH_2SO_3X$; $Y_4$ is —H or Br; $Y_5$ is —H, —Cl or —Br; $Y_6$ is —Br or —$OSO_3X$; R is —H, —$CH_3$ or —$C_2H_5$; X is —H, —Na or —K.

The present invention provides protein macromolecular dyes wherein dye B which can react with the protein macromolecules including natural protein macromolecules such as casein, gelatin, fur-protein, and the modified protein macromolecules according to formula (2) and (10) is the azo metal complex dye which has the structure

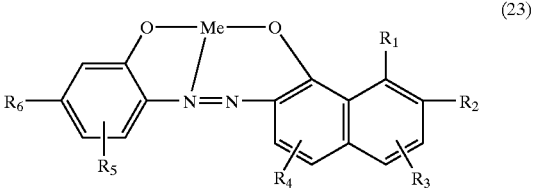
(23)

wherein Me is Cu, Co, Ni or Cr; $R_1$, $R_2$, $R_3$, $R_4$, $R_5$ and $R_6$ each represents respectively —H, —Cl, —$CH_3$, —$OCH_3$, —$SO_3X$, —COOX, —$CH_2SO_3X$, —$NH_2$, —$N(CH_3)_2$,

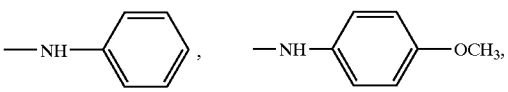

—$NHCOCH_3$, —$NHCONH_2$,

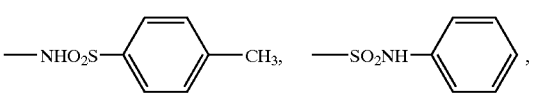

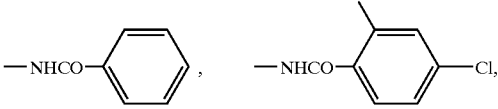

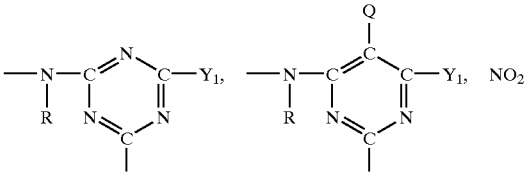

—$SO_2CH_2CH_2Y_3$, —$SO_2NHCH_2CH_2Y_3$,

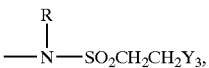

—$NHCOCY_4$=$CHY_5$, or —$NHCOCHY_4CH_2Y_6$; wherein $Y_1$ is —Cl, —F or —$CH_3$; Q is —Cl, —$CH_3$; $Y_2$ is —Cl, —F, —R, —OR, —$NHCH_2SO_3X$,

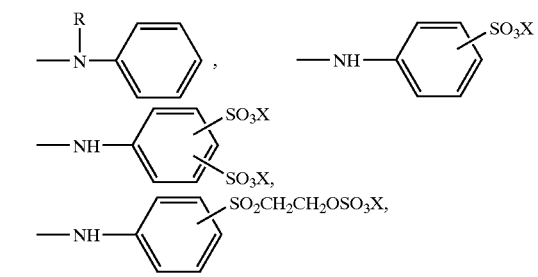

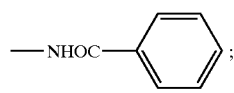

—N(R)$_2$, —N(CH$_2$OH)$_2$, —N(C$_2$H$_4$OH)$_2$, —SO$_2$R,

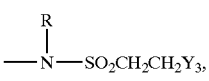

Y$_3$ is —Cl, —OSO$_3$X or —N(CH$_3$)CH$_2$CH$_2$SO$_3$X; Y$_4$ is —H or —Br; Y$_5$ is —H, —Cl or —Br; Y$_6$ is —Br or —OSO$_3$X; R is —H, —CH$_3$ or —C$_2$H$_5$; X is —H, —Na or —K.

The present invention provides protein macromolecular dyes wherein dye B which can react with the protein macromolecules including natural protein macromolecules such as casein, gelatin, fur-protein, and the modified protein macromolecules according to formula (2) and (10) is the azo metal complex dye which has the structure

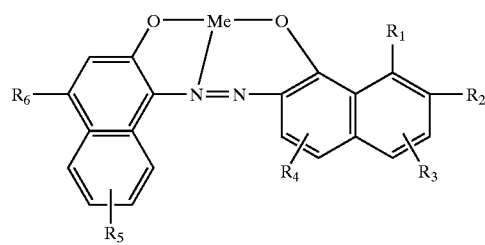

(24)

wherein Me is Cu, Co, Ni or Cr; R$_1$, R$_2$, R$_3$, R$_4$, R$_5$ and R$_6$ each represents respectively —H, —Cl, —CH$_3$, —OCH$_3$, —SO$_3$X, —COOX, —CH$_2$SO$_3$X, —NH$_2$, —N(CH$_3$)$_2$,

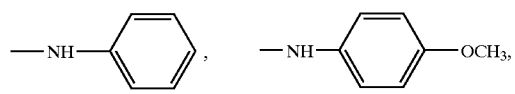

—NHCOCH$_3$, —NHCONH$_2$,

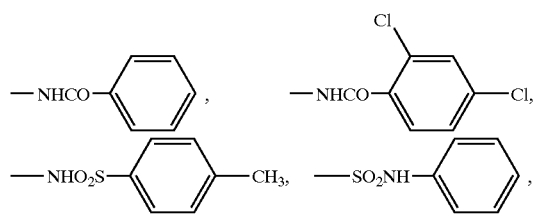

-continued

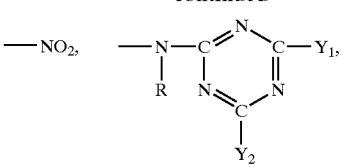

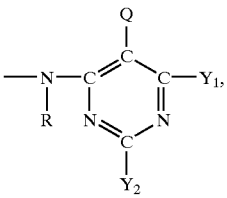

—SO$_2$CH$_2$CH$_2$Y$_3$,

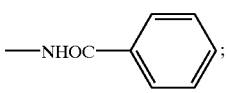

—SO$_2$NHCH$_2$CH$_2$Y$_3$, —NHCOCY$_4$=CHY$_5$, or —NHCOCHY$_4$CH$_2$Y$_6$; wherein Y$_1$ is —Cl, —F or —CH$_3$; Q is —Cl, —CH$_3$; Y$_2$ is —Cl, —F, —R, —OR, —NHCH$_2$SO$_3$X,

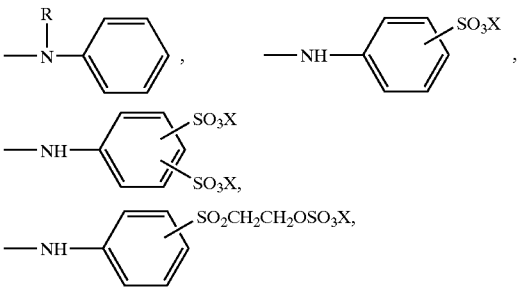

—N(R)$_2$, —N(C$_2$H$_4$OH)$_2$, —N(CH$_2$OH)$_2$, —SO$_2$R,

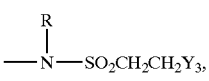

Y$_3$ is —Cl, —OSO$_3$X or —N(CH$_3$)CH$_2$CH$_2$SO$_3$X; Y$_4$ is —H or Br; Y$_5$ is —H, —Cl or —Br; Y$_6$ is —Br or —OSO$_3$X; R is —H, —CH$_3$ or —C$_2$H$_5$; X is —H, —Na or —K.

The present invention provides protein macromolecular dyes wherein dye B which can react with the protein macromolecules including natural protein macromolecules such as casein, gelatin, fur-protein, and the modified protein macromolecules according to formula (2) and (14) is the anthraquinone dye which has the structure

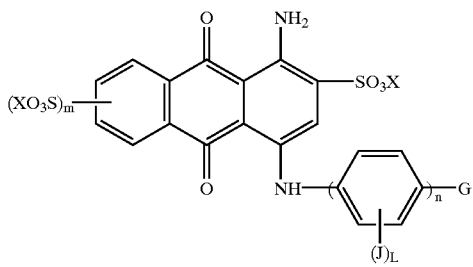

(25)

wherein m or n is 0 or 1 respectively; L is 0, 1, 2, or 3; J is —CH₃, —Cl, —SO₃X; G is

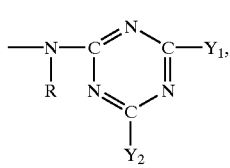 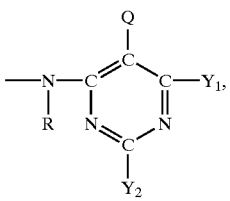

—SO₂CH₂CH₂Y₃,

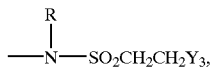

—SO₂NHCH₂CH₂Y₃, —NHCOCY₄=CHY₅, or —NHCOCHY₄CH₂Y₆; wherein Y₁ is —Cl, —F or —CH₃; Q is —Cl, —CH₃; Y₂ is —Cl, —F, —R, —OR, —NHCH₂SO₃X,

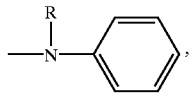

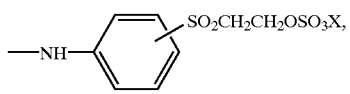

—N(CH₂OH)₂, —N(C₂H₄OH)₂, —N(R)₂, —SO₂R,

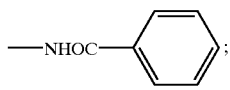

Y₃ is —Cl, —OSO₃X or —N(CH₃)CH₂CH₂SO₃X; Y₄ is —H or Br; Y₅ is —H, —Cl or —Br; Y₆ is —Br or —OSO₃X; R is —H, —CH₃ or —C₂H₅; X is —H, —Na or —K.

An embodiment of the present invention is described in detail as follows:

The present invention provides a synthesis process for protein macromolecular dyes in which protein macromolecules consisting of amino acids or the modified protein macromolecules is reacted with azo dyes, azo metal complex dyes, anthraquinone dyes at pH ranging from 2–12, the former is used as macromolecular backbone, the latter bears the reactive groups such as halotriazinyl, halopyrimidinyl, ethylsulphonyl, N-ethyl aminosulfonyl, N-ethyl sulfonylamino, (N-vinylcarbonyl)amino, propionamido and their derivatives.

The structure of the protein macromolecular dyes may be expressed as follows:

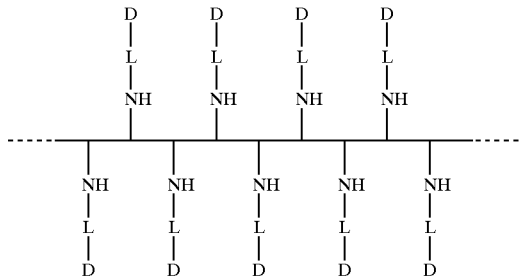

Wherein - - - - is the protein macromolecules or modified protein macromolecules as the polymeric support matrix; L is the linking group including triazinyl, pyrimidinyl, ethylsulfonyl, N-ethyl aminosulfonyl, N-ethylsulfonylamino, (N-vinylcarbonyl)amino, propionamido and their derivatives; D is a parent dye including the azo dye, azo metal complex dye and anthraquinone dye.

There are abundant reactive amino groups in the protein macromolecules including the natural protein macromolecules consisting of amino acids and the modified protein macromolecules. The protein macromolecular dyes can be prepared by the reaction between the amino groups of the protein macromolecules and the reactive groups of the dyes. The processes are completed according to the equations as follows:

(1) The dyes with halotriazinyl reactive groups or their derivatives, react with the amino groups of the protein macromolecules or modified protein macromolecules on the basis of a nucleophilic substitution reaction:

(E1)

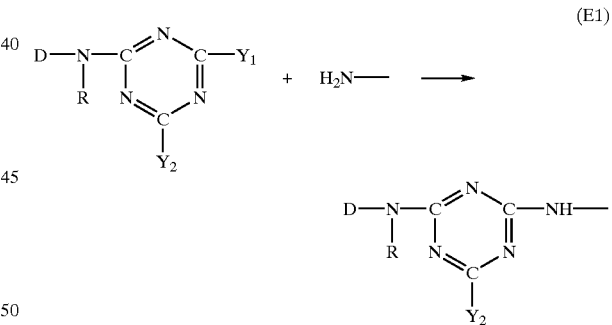

wherein Y₁ is —Cl, —F or —CH₃; Y₂ is —Cl, —F, —R, —OR, —NHCH₂SO₃X,

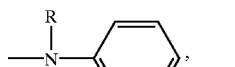

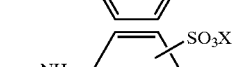

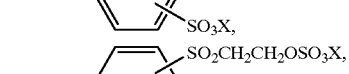

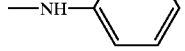

—N(R)$_2$, —N(CH$_2$OH)$_2$, —N(C$_2$H$_4$OH)$_2$, —SO$_2$R,

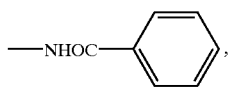

R is —H, —CH$_3$ or —C$_2$H$_5$; X is —H, —Na or —K; D is the parent dye including azo dyes, azo metal complex dyes and anthraquinone dyes.

(2) The dyes with halopyrimidinyl reactive groups or their derivatives, react with the amino groups of the protein macromolecules and modified protein macromolecules on the basis of a nucleophilic substitution reaction:

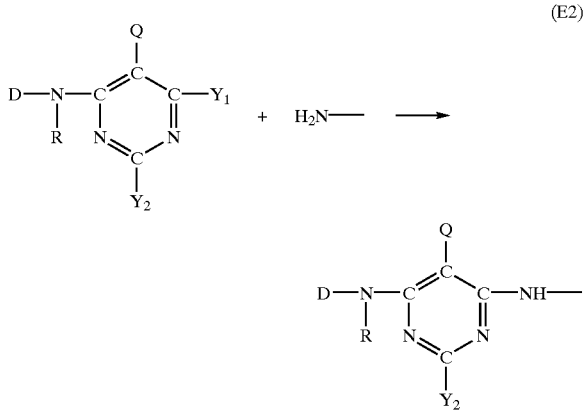
(E2)

wherein Y$_1$ is —Cl, —F or —CH$_3$; Q is —Cl, or —CH$_3$; Y$_2$ is —Cl, —F, —R, —OR, —SO$_2$R, —NHCH$_2$SO$_3$X, —N(R)$_2$, —N(CH$_2$OH)$_2$, —N(C$_2$H$_4$OH)$_2$,

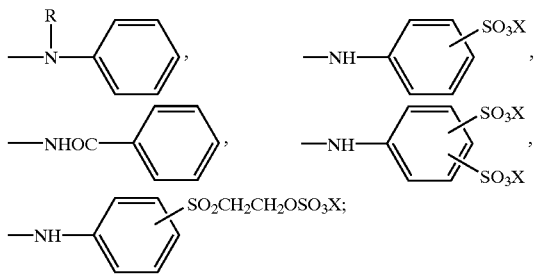

R is —H, —CH$_3$ or —C$_2$H$_5$; X is —H, —Na or —K; D is the parent dye including azo dyes, azo metal complex dyes and anthraquinone dyes.

(3) The dyes with ethylsulfonyl, N-ethyl aminosulfonyl, N-ethylsulfonylamino reactive groups or their derivatives, react with the amino groups of the protein macromolecules and modified protein macromolecules on the basis of elimination-addition reaction:

a. The elimination reactions are completed respectively as follows:

(E3)

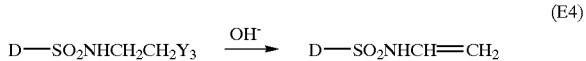
(E4)

$$D\text{—}N(R)\text{—}SO_2CH_2CH_2Y_3 \xrightarrow{OH^-} D\text{—}N(R)\text{—}SO_2CH\text{=}CH_2$$ (E5)

b. The additions with the amino groups are completed respectively as follows:

D—SO$_2$CH=CH$_2$ + NH— ⟶ D—SO$_2$CH$_2$CH$_2$NH— (E6)

D—SO$_2$NHCH=CH$_2$ + NH— ⟶ D—SO$_2$NHCH$_2$CH$_2$NH— (E7)

D—N(R)—SO$_2$CH=CH$_2$ + NH— ⟶ D—N(R)—SO$_2$CH$_2$CH$_2$NH— (E8)

wherein Y$_3$ is —Cl, —OSO$_3$X or —N(CH$_3$)CH$_2$CH$_2$SO$_3$X; R is —H, —CH$_3$ or —C$_2$H$_5$; X is —H, —Na or —K; D is the parent dye including azo dyes, azo metal complex dyes and anthraquinone dyes.

(4) The dyes with (N-vinylcarbonyl)amino or their derivatives, react with the amino groups of the protein macromolecules and modified protein macromolecules on the basis of a reaction as follows:

The molecular formula of the dye containing (N-vinylcarbonyl)amino or its derivatives is expressed as follows:

D—NHCO—CY$_4$=CHY$_5$ a. when Y$_4$ is —H; Y$_5$ is —H or —Cl, the nucleophilic addition reactions are completed as follows:

D—NHCO—CH=CH$_2$+NH—→D—NHCOCH$_2$CH$_2$—NH— (E9)

D—NH—CO—CH=CHCl+NH—→D—NHCOCH$_2$CHCl—NH— (E10)

b. when Y$_4$ is —Br; Y$_5$ is —H, the addition-substitution reactions are completed as follows:

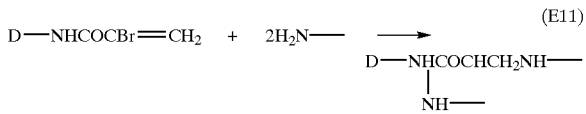
(E11)

c. when Y$_4$ and Y$_5$ both represent —Br, the elimination-addition-substitution reaction is completed as follows:

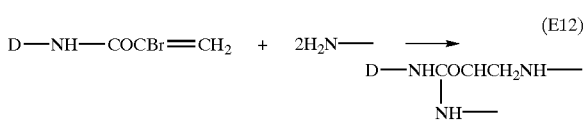
(E12)

wherein D are the parent dyes including the azo dyes, azo metal complex dyes and anthraquinone dyes.

(5) The dyes with propionamido and its derivatives, react with the amino groups of the protein macromolecules or modified protein macromolecules on the basis of the reaction as follows:

The molecular formula of the dye containing propionamido or its derivatives is expressed as follows:

D—NHCOCHY$_4$CH$_2$Y$_6$ a. When Y$_4$ is —H, Y$_6$ is —OSO$_3$X, the elimination-addition reactions are completed as follows:

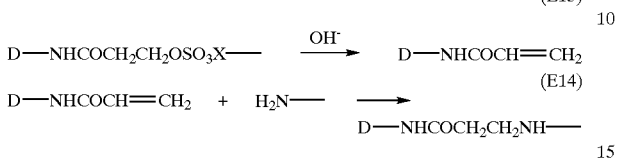

(E13) D—NHCOCH$_2$CH$_2$OSO$_3$X— $\xrightarrow{OH^-}$ D—NHCOCH=CH$_2$ (E14) D—NHCOCH=CH$_2$ + H$_2$N— → D—NHCOCH$_2$CH$_2$NH— b. When Y$_4$ and Y$_6$ both represent —Br, the elimination-addition-substitution reactions are completed as follows:

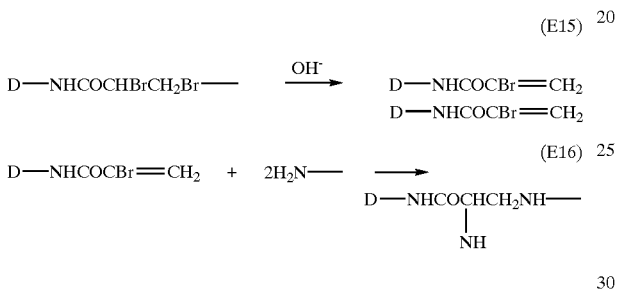

(E15) D—NHCOCHBrCH$_2$Br— $\xrightarrow{OH^-}$ D—NHCOCBr=CH$_2$
D—NHCOCBr=CH$_2$ (E16) D—NHCOCBr=CH$_2$ + 2H$_2$N— → D—NHCOCHCH$_2$NH—
                                                    |
                                                    NH wherein D are the parent dyes including the azo dyes, azo metal complex dyes and anthraquinone dyes.

The present invention provides the natural protein macromolecules as the polymeric support matrix. The natural protein macromolecules consisting of the amino acids include gelatin prepared by the bone, skin, tendon, horn core of big mammals; casein prepared by the milk of big mammals and fur-protein prepared by fur-fabric of mammals.

The reactive groups of the dyes reacting with the amino groups of the protein macromolecules have the structure (1) (F1)

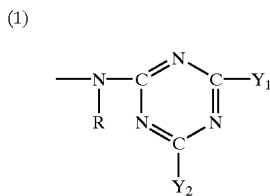

wherein Y$_1$ is —Cl, —F or —CH$_3$; Y$_2$ is —Cl, —F, —R, —OR, —NHCH$_2$SO$_3$X,

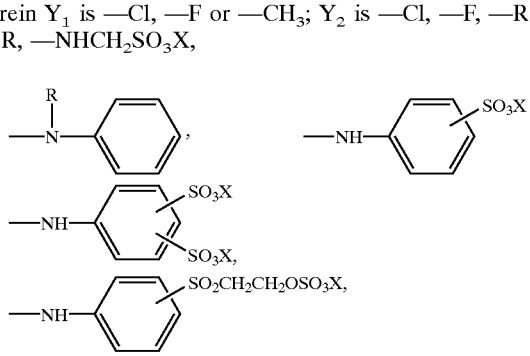

—N(R)$_2$, —N(CH$_2$OH)$_2$, —N(C$_2$H$_4$OH)$_2$, —SO$_2$R,

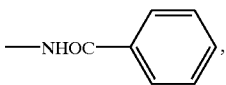

R is —H, —CH$_3$ or —C$_2$H$_5$; X is —H, —Na or —K.

(2) (F2)

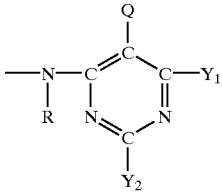

wherein Y$_1$ is —Cl, —F or —CH$_3$; Q is —Cl, or —CH$_3$; Y$_2$ is —Cl, —F, —R, —OR, —NHCH$_2$SO$_3$X, or

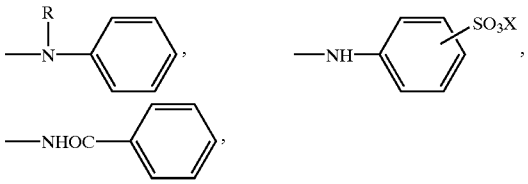

—N(R)$_2$, —N(CH$_2$OH)$_2$, —N(C$_2$H$_4$OH)$_2$, —SO$_2$R,

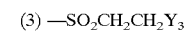

R is —H, —CH$_3$ or —C$_2$H$_5$; X is —H, —Na or —K.

(3) —SO$_2$CH$_2$CH$_2$Y$_3$ (F3)

wherein Y$_3$ is —Cl, —OSO$_3$X, or —N(CH$_3$)CH$_2$CH$_2$SO$_3$X; X is —H, —Na, or —K.

(4) —SO$_2$NHCH$_2$CH$_2$Y$_3$ (F4)

wherein Y$_3$ is —Cl, —OSO$_3$X, or —N(CH$_3$)CH$_2$CH$_2$SO$_3$X; X is —H, —Na, or —K.

(5) —N—SO$_2$CH$_2$CH$_2$Y$_3$ (F5)
    |
    R wherein Y$_3$ is —Cl, —OSO$_3$X, or —N(CH$_3$)CH$_2$CH$_2$SO$_3$X; R is —H, —CH$_3$, or —C$_2$H$_5$; X is —H, —Na or —K.

(6) —NHCOCY$_4$=CHY$_5$ (F6)

wherein Y$_4$ is —H, or —Br; Y$_5$ is —H, —Cl, or —Br.

(7) —NHCOCHY$_4$CH$_2$Y$_6$ (F7)

wherein Y$_4$ is —H, or —Br; Y$_6$ is —Br, or —OSO$_3$X; X is —H, —Na, or —K.

The present invention provides the modified protein macromolecules used as the polymeric support matrix. The modified protein macromolecules have the structure A'(D)$_d$ wherein A' are the modified protein macromolecules derived from the protein macromolecules A of which 0.1~95% amino groups are substituted by the dyes, d are integers between 1~2400, D are single or mixed groups as follows:

(1)

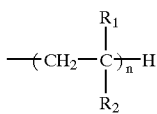

wherein $R_1$ is —H or —$CH_3$; n are integers between 1~1000; $R_2$ is —COOH, —$CONH_2$, —CN, —$COOCH_3$, —$COOC_2H_5$, —$COOC_3H_7$, —$COOC_4H_9$, —Cl, —CHO, —$COOC_2H_4OH$, or

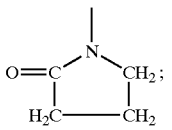

(2)

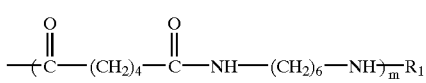

wherein m are integers between 1~200; $R_1$ is —H,

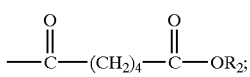

$R_2$ is —H, —$CH_3$, —$C_2H_5$;

(3)

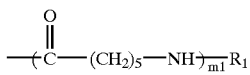

wherein $m_1$ are integers between 1~300; $R_1$ is —H, or

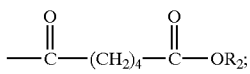

$R_2$ is —H, —$CH_3$, or —$C_2H_5$.

The modified protein macromolecules are prepared by solution polymerization, emulsion polymerization, suspension polymerization or polycondensation between monomers and the natural protein macromolecules such as casein, gelatin and fur-protein. The monomers may be a single or mixed compounds of acrylic acid, methacrylic acid, acrylamide, methylacrylamide, acrylonitrile, methylacrylonitrile, methyl acrylate, methyl methacrylate, ethyl acrylate, methyl ethylacrylate, propyl acrylate, methyl propyl acrylate, butyl acrylate, methyl butylacrylate, vinyl chloride, acrolein, (2-hydroxyl)ethylacrylate, styrene, 2-vinylpyridine, vinylpyrrolidone, caprolactam, adipic acid and hexadiamine. The modified protein macromolecules also may be prepared by a condensation reaction of polyamide and the protein macromolecules including casein, gelatin, and fur-protein.

The reactive groups of the dyes, which can react with the amino groups of the modified protein macromolecules, have the structure (1)

(F1)

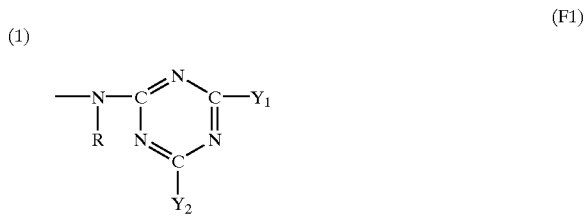

wherein $Y_1$ is —Cl, —F or —$CH_3$; $Y_2$ is —Cl, —F, —R, —OR, —$NHCH_2SO_3X$,

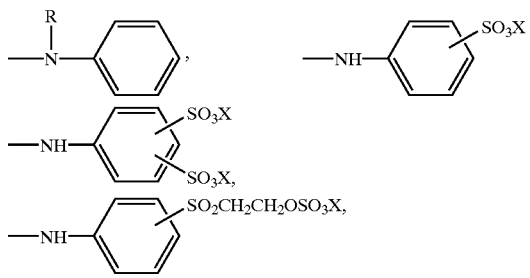

—$N(R)_2$, —$N(CH_2OH)_2$, —$N(C_2H_4OH)_2$, —$SO_2R$,

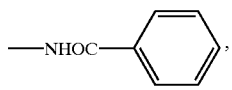

R is —H, —$CH_3$ or —$C_2H_5$; X is —H, —Na or —K.

(2)

(F2)

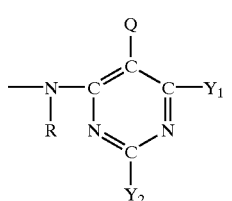

wherein $Y_1$ is —Cl, —F or —$CH_3$; Q is —Cl, —$CH_3$; $Y_2$ is —Cl, —F, —R, —OR, —$NHCH_2SO_3X$,

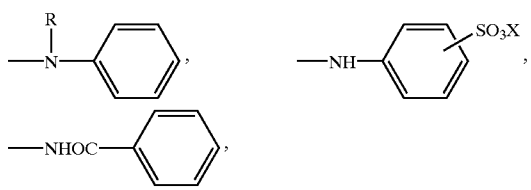

—$N(R)_2$, —$N(CH_2OH)_2$, —$N(C_2H_4OH)_2$, —$SO_2R$,

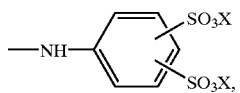

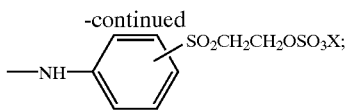

R is —H, —CH₃ or —C₂H₅; X is —H, —Na or —K.

(3) —SO₂CH₂CH₂Y₃ (F3)

wherein $Y_3$ is —Cl, —OSO₃X, or —N(CH₃)CH₂CH₂SO₃X; X is —H, —Na, or —K.

(4) —SO₂NHCH₂CH₂Y₃ (F4)

wherein $Y_3$ is —Cl, —OSO₃X, or —N(CH₃)CH₂CH₂SO₃X; X is —H, —Na, or —K.

(5) (F5)

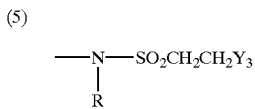

wherein $Y_3$ is —Cl, —OSO₃X, or —N(CH₃)CH₂CH₂SO₃X; R is —H, —CH₃, or —C₂H₅; X is —H, —Na, or —K.

(6) —NHCOCY₄=CHY₅ (F6)

wherein $Y_4$ is —H, or —Br; $Y_5$ is —H, —Cl, or —Br.

(7) —NHCOCHY₄CH₂Y₆ (F7)

wherein $Y_4$ is —H, or —Br; $Y_6$ is —Br, or —OSO₃X; X is —H, —Na, or —K.

In the present invention, the parent dyes are the azo dyes, azo metal complex dyes and anthraquinone dyes which can react with the amino groups of the protein macromolecules or modified protein macromolecules.

The azo dyes have three kinds of structures($D_1$, $D_2$, $D_3$)

(1) (D1)

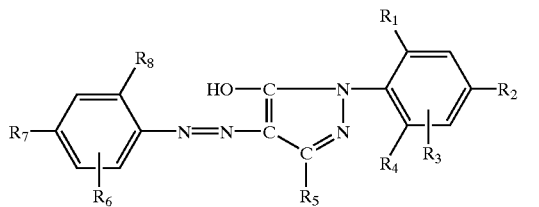

wherein $R_1$, $R_4$ and $R_8$ each represents —H, —Cl, —CH₃, —OCH₃, —OH, —COOX or —SO₃X respectively; $R_5$ is —H, —CH₃, —COOX, —SO₃X, —SO₂NH₂, or

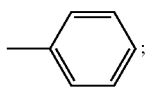;

$R_2$, $R_3$, $R_6$ and $R_7$ each represents respectively —H, —Cl, —CH₃, —SO₃X, —COOX, —OCH₃, —NO₂, —SO₂NHR,

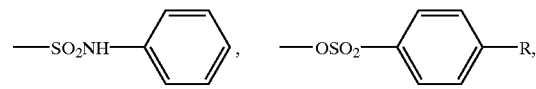

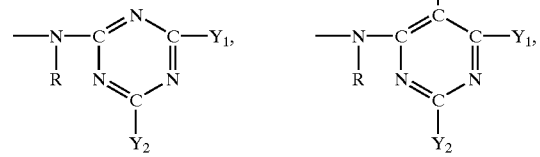

—SO₂CH₂CH₂Y₃,

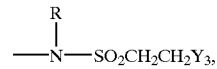

—SO₂NHCH₂CH₂Y₃, —NHCOCY₄=CHY₅, or —NHCOCHY₄CH₂Y₆; wherein $Y_1$ is —Cl, —F or —CH₃; Q is —Cl, —CH₃; $Y_2$ is —Cl, —F, —R, —OR, —NHCH₂SO₃X,

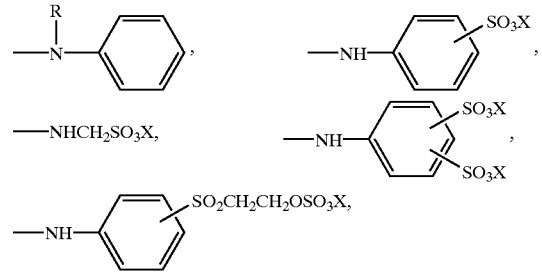

—NHCH₂SO₃X,

—N(R)₂, —N(C₂H₄OH)₂, —N(CH₂OH)₂, —SO₂R,

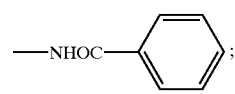;

$Y_3$ is —Cl, —OSO₃X or —N(CH₃)CH₂CH₂SO₃X; $Y_4$ is —H or —Br; $Y_5$ is —H, —Cl or —Br; $Y_6$ is —Br or —OSO₃X; R is —H, —CH₃ or —C₂H₅; X is —H, —Na or —K.

(2) (D2)

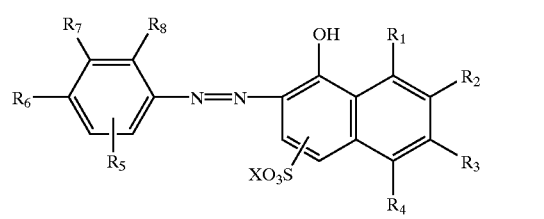

wherein $R_4$, $R_7$ and $R_8$ each represents —H, —CH₃, —OH, —OCH₃, —NO₂, —SO₃X, or —COOX respectively; $R_1$, $R_2$, $R_3$, $R_5$ and $R_6$ each represents respectively —H, —Cl, —CH₃, —OR, —SO₃X, —COOX, —CH₂SO₃X, —NO₂, —N(R)₂,

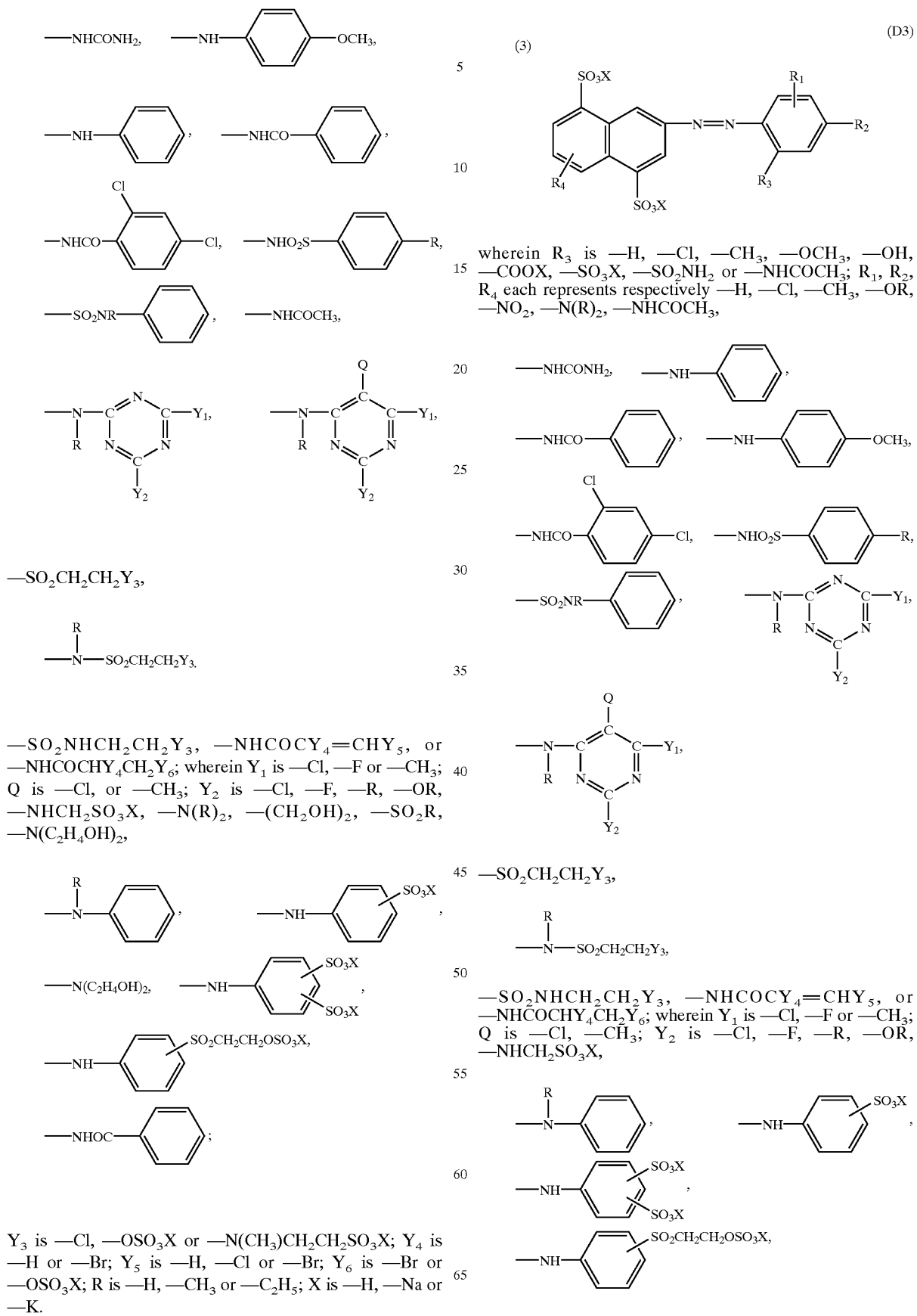

—N(R)$_2$, —N(CH$_2$OH)$_2$, —N(C$_2$H$_4$OH)$_2$, —SO$_2$R,

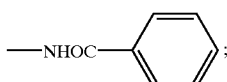

$Y_3$ is —Cl, —OSO$_3$X or —N(CH$_3$)CH$_2$CH$_2$SO$_3$X; $Y_4$ is —H or —Br; $Y_5$ is —H, —Cl or —Br; $Y_6$ is —Br or —OSO$_3$X; R is —H, —CH$_3$ or —C$_2$H$_5$; X is —H, —Na or —K.

The azo metal complex dyes have four kinds of structures ($D_4$, $D_5$, $D_6$, $D_7$)

(1) (D4)

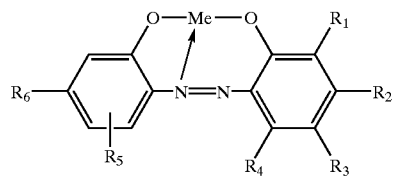

(2) (D5)

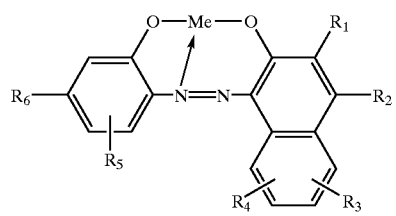

(3) (D6)

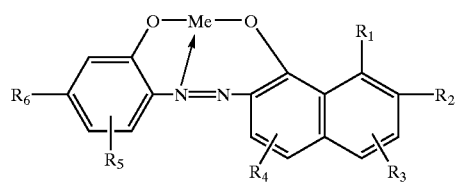

(4) (D7)

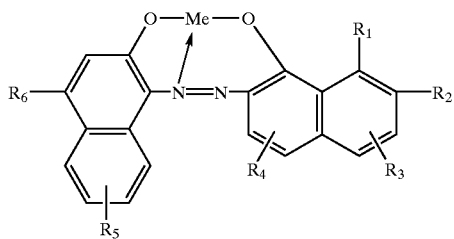

wherein Me is Cu, Co, Ni and Cr; $R_1$, $R_2$, $R_3$, $R_4$, $R_5$ and $R_6$ each represents respectively —H, —Cl, —CH$_3$, —OCH$_3$, —SO$_3$X, —COOX, —CH$_2$SO$_3$X, —NH$_2$, —N(CH$_3$)$_2$, —NHCOCH$_3$, —NHCONH$_2$,

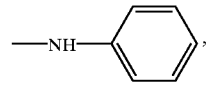 , 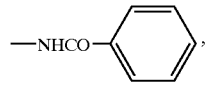 ,

-continued

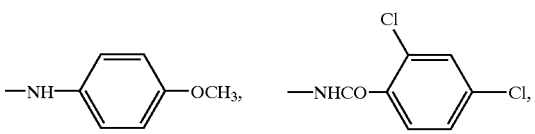

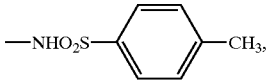 , 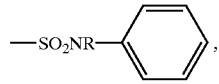 ,

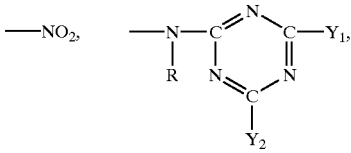

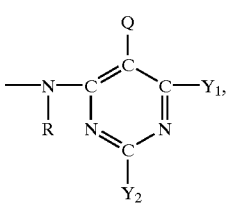

—SO$_2$CH$_2$CH$_2$Y$_3$,

—SO$_2$NHCH$_2$CH$_2$Y$_3$, —NHCOCY$_4$=CHY$_5$, or —NHCOCHY$_4$CH$_2$Y$_6$; wherein Y$_1$ is —Cl, —F or —CH$_3$; Q is —Cl, —CH$_3$; Y$_2$ is —Cl, —F, —R, —OR, —NHCH$_2$SO$_3$X,

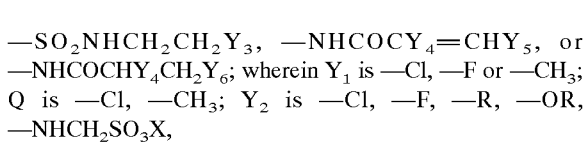

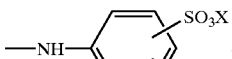

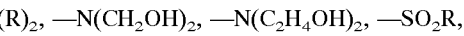

—N(R)$_2$, —N(CH$_2$OH)$_2$, —N(C$_2$H$_4$OH)$_2$, —SO$_2$R,

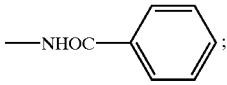

$Y_3$ is —Cl, —OSO$_3$X or —N(CH$_3$)CH$_2$CH$_2$SO$_3$X; $Y_4$ is —H or —Br; $Y_5$ is —H, —Cl or —Br; $Y_6$ is —Br or —OSO$_3$X; R is —H, —CH$_3$ or —C$_2$H$_5$; X is —H, —Na or —K.

The anthraquinone dyes have one kind of structure ($D_8$)

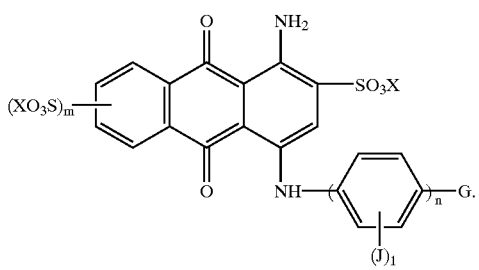

(D8)

wherein m or n is 0 or 1 respectively; L is 0, 1, 2, or 3; J is —$CH_3$, —Cl, —$SO_3X$; G is

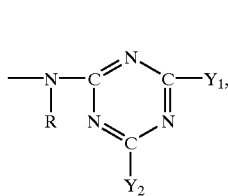 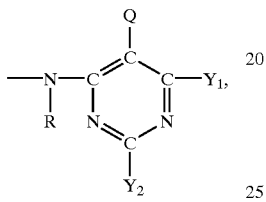

—$SO_2CH_2CH_2Y_3$,

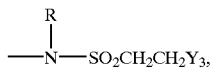

—$SO_2NHCH_2CH_2Y_3$, —$NHCOCY_4$=$CHY_5$, or —$NHCOCHY_4CH_2Y_6$; wherein $Y_1$ is —Cl, —F or —$CH_3$; Q is —Cl, —$CH_3$; $Y_2$ is —Cl, —F, —R, —OR, —$NHCH_2SO_3X$,

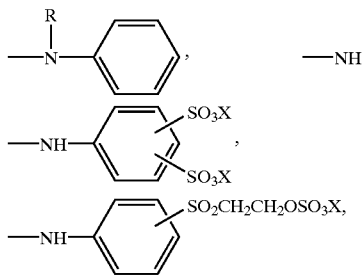

—$N(R)_2$, —$N(CH_2OH)_2$, —$N(C_2H_4OH)_2$, —$SO_2R$,

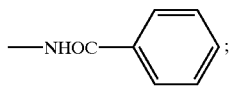;

$Y_3$ is —Cl, —$OSO_3X$ or —$N(CH_3)CH_2CH_2SO_3X$; $Y_4$ is —H or —Br; $Y_5$ is —H, —Cl or —Br; $Y_6$ is —Br or —$OSO_3X$; R is —H, —$CH_3$ or —$C_2H_5$; X is —H, —Na or —K.

In the present invention, the preparation method of the protein macromolecular dyes can be divided into several groups according to the reactive groups of the dyes, which can react with the amino groups of the protein macromolecules.

(1) When the reactive group of the parent dyes is halotriazinyl:

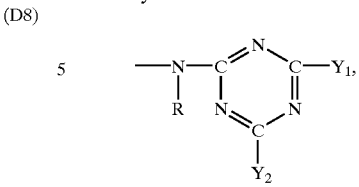

wherein $Y_1$ is —Cl, —F or —$CH_3$; $Y_2$ is —Cl, —F, —R, —OR, —$NHCH_2SO_3X$,

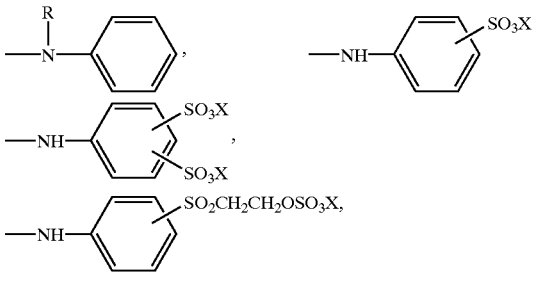

—$N(R)_2$, —$N(CH_2OH)_2$, —$N(C_2H_4OH)_2$, —$SO_2R$,

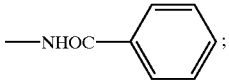;

R is —H, —$CH_3$ or —$C_2H_5$; X is —H, —Na or —K; the protein macromolecular dyes can be prepared as follows:

(a) When $Y_1$ is —Cl or —F, $Y_2$ is —Cl or —F: the protein macromolecular or modified protein macromolecular dyes can be obtained by the following reaction. A mixture of 1000 parts by weight protein macromolecules or modified protein macromolecules, 1000~200000 parts by weight $H_2O$ and 100~2000 parts by weight dyes with halotriazinyl reactive groups, which include azo dyes, azometal dyes and anthraquinone dyes, is heated to 30~85° C. in pH 2~12 for 1~10 hours. 100~1000 parts by weight dyes, 5000~200000 parts by weight $H_2O$, the range of 35~70° C. and pH 3~10 are preferred. The pH is adjusted with acid or base which may be any one of $H_3CCOONa$, $ClH_2CCOONa$, $Cl_2HCCOONa$, $Cl_3CCOONa$, $Na_2CO_3$, $NaHCO_3$, NaOH, $Na_2B_4O_7 \cdot 10H_2O$, $NaH_2PO_4$ and $Na_2HPO_4$.

(b) When $Y_1$ is —Cl, —F or —$CH_3$; $Y_2$ is —R, —OR, —$NHCH_2SO_3X$,

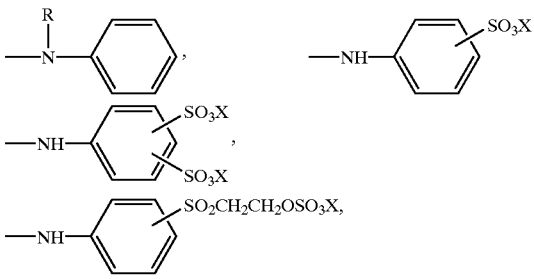

—N(R)$_2$, —N(CH$_2$OH)$_2$, —N(C$_2$H$_4$OH)$_2$, —SO$_2$R,

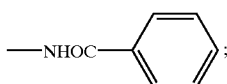

R is —H, —CH$_3$ or —C$_2$H$_5$; X is —H, —Na or —K; the protein macromolecular dyes can be prepared as follows:

A mixture of 1000 part in weight protein macromolecules or modified protein macromolecules, 1000~200000 part in weight H$_2$O and 100~2000 part in weight dyes with halotriazinyl reactive groups, which include azo dyes, azometal dyes and anthraquinone dyes, is heated to 30~85° C. in pH 2~12 for 1~10 hours. 100~1000 parts by weight dyes, 5000~200000 parts by weight H$_2$O, the range of 60~85° C. and pH 3~10 are preferred. The pH is adjusted with acid or base which may be any one of H$_3$CCOONa, ClH$_2$CCOONa, Cl$_2$HCCOONa, Cl$_3$CCOONa, Na$_2$CO$_3$, NaHCO$_3$, NaOH, Na$_2$B$_4$O$_7$10H$_2$O, NaH$_2$PO$_4$ and Na$_2$HPO$_4$.

(2) When the reactive groups of the parent dyes are halopyrimidinyl:

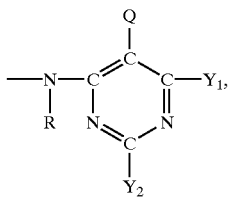

wherein Y$_1$ is —Cl, —F or —CH$_3$; Q is —Cl, —CH$_3$; Y$_2$ is —Cl, —F, —R, —OR, —NHCH$_2$SO$_3$X,

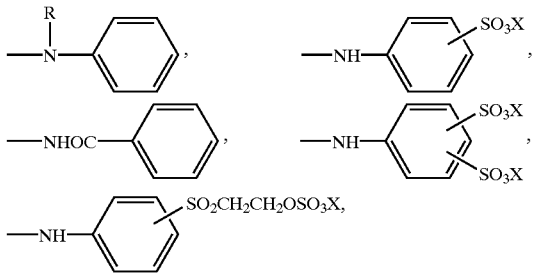

—N(R)$_2$, —N(CH$_2$OH)$_2$, —N(C$_2$H$_4$OH)$_2$, —SO$_2$R, R is —H, —CH$_3$ or —C$_2$H$_5$; X is —H, —Na or —K.

(a) when Y$_1$ is —Cl or —F, Y$_2$ is —Cl or —F: the protein macromolecular or modified protein macromolecular dyes can be obtained by the following reaction. A mixture of 1000 parts by weight protein macromolecules or modified protein macromolecules, 1000~200000 parts by weight H$_2$O and 100~2000 parts by weight dyes with halotriazinyl reactive groups, which include azo dyes, azometal dyes and anthraquinone dyes, is heated to 30~85° C. in pH 2~12 for 1~10 hours. 100~1000 parts by weight dyes, 5000~200000 parts by weight H$_2$O, the range of 35~70° C. and pH 3~10 are preferred. The pH is adjusted with acid or base which may be any one of H$_3$CCOONa, ClH$_2$CCOONa, Cl$_2$HCCOONa, Cl$_3$CCOONa, Na$_2$CO$_3$, NaHCO$_3$, NaOH, Na$_2$B$_4$O$_7$ 10H$_2$O, NaH$_2$PO$_4$, Na$_2$HPO$_4$.

(b) When Y$_1$ is —Cl, —F or —CH$_3$; Q is —Cl, —F, —CH$_3$; Y$_2$ is —R, —OR, —NHCH$_2$SO$_3$X,

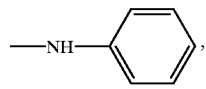 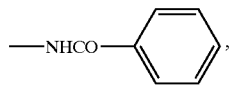

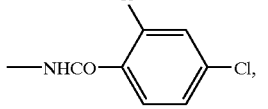 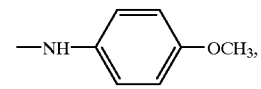

—N(R)$_2$, —N(CH$_2$OH)$_2$, —N(C$_2$H$_4$OH)$_2$, —SO$_2$R, R is —H, —CH$_3$ or —C$_2$H$_5$; X is —H, —Na or —K; the protein macromolecular dyes can be prepared as follows:

A mixture of 1000 parts by weight protein macromolecules or modified protein macromolecules, 1000~200000 parts by weight H$_2$O and 100~2000 parts by weight dyes with halotriazinyl reactive groups, which include azo dyes, azo metal dyes and anthraquinone dyes, is heated to 30~85° C. in pH 2~12 for 1~10 hours. 100~1000 parts by weight dyes, 5000~200000 parts by weight H$_2$O, the range of 60~85° C. and pH 3~10 are preferred. The pH is adjusted with acid or base which may be any one of H$_3$CCOONa, ClH$_2$CCOONa, Cl$_2$HCCOONa, Cl$_3$CCOONa, Na$_2$CO$_3$, NaHCO$_3$, NaOH, Na$_2$B$_4$O$_7$ 10H$_2$O, NaH$_2$PO$_4$, Na$_2$HPO$_4$.

(3) When the reactive groups of the parent dyes are expressed as follows:

wherein Y$_3$ is —Cl, —OSO$_3$X or —N(CH$_3$)CH$_2$CH$_2$SO$_3$X; Y$_4$ is —H or —Br; Y$_5$ is —H, —Cl or —Br; Y$_6$ is —Br or —OSO$_3$X; R is —H, —CH$_3$ or —C$_2$H$_5$; X is —H, —Na or —K; the protein macromolecular dyes can be prepared as follows:

A mixture of 1000 parts by weight protein macromolecules or modified protein macromolecules, 1000~200000 parts by weight H$_2$O and 100~2000 parts by weight dyes with halotriazinyl reactive groups, which include azo dyes, azo metal dyes and anthraquinone dyes, is heated to 30~85° C. in pH 2~12 for 1~10 hours. 100~1000 parts by weight dyes, 5000~200000 parts by weight H$_2$O, the range of 50~80° C. and pH 3~10 are preferred. The pH is adjusted with acid or base which may be any one of H$_3$CCOONa, ClH$_2$CCOONa, Cl$_2$HCCOONa, Cl$_3$CCOONa, Na$_2$CO$_3$, NaHCO$_3$, NaOH, Na$_2$B$_4$O$_7$ 10H$_2$O, NaH$_2$PO$_4$, Na$_2$HPO$_4$.

The protein macromolecular dyes may be used in dyeing protein materials such as leather, silk and wool.

In general, leather is first dyed by acid dyes, direct dyes or reactive dyes, then coated by a coating agent. When acid dyes or direct dye is used in dyeing leather, the fastness is usually 3~4 grade. And reactive dye is not friendly to the environment because of the low reactivity of the dye. During the finishing process, membrane-forming agent, pigment paste and other additives are often necessary in the coating agent after the leather is dyed.

The present invention provides the protein macromolecular dyes of good properties. Because abundant parent dyes are linked to protein macromolecular support matrix, the dyes not only have bright color like acid dyes, direct dyes and reactive dyes, but also increased color brightness. The fastness thereof is higher than that of acid and direct dyes because the macromolecules may be crosslinked by crosslinking agents. The fixation of the protein macromolecular dyes in dyeing leather is much higher than that of conventional acid dyes, direct dyes and reactive dyes because the structure of the protein macromolecular dyes is similar to protein material such as leather. Therefore, the dyeing process in which the protein macromolecular dyes are used on the leather has very low environmental pollution. The protein macromolecular dyes are of compatibility, ability of filling and membrane-forming the common properties of macromolecular material. So they can be used in protein material staining as novel dyes which can complete dyeing, coating and membrane-forming in one step.

The conversion of the dyes is above 90% in the present, process for preparing protein macromolecule because the chemical reaction of dyes with protein macromolecule or modified protein macromolecule is performed in homogeneous solution, and it can be above 95% by changing the ratio of the dyes to protein macromolecule in accordance with the structures of the dyes. The content of the parent dyes on the macromolecule support matrix (in weight) is above 20%, and it can be 50% by changing the ratio of the dyes to protein macromolecule. The obtained macromolecular dyes can be formulated into products in different amount.

During the dyeing process, the protein macromolecular dyes are absorbed on the surface of leather, diffused to the inner part and crosslinked by using crosslinking agent so as to be fastened.

The protein macromolecular dyes have bright colors like acid dyes, direct dyes and reactive dyes. Their fixation is above 95% when they are applied in dyeing leather. The dry and wet fastness of the leather dyed by the protein macromolecular dyes are 5 and 4~5 degree respectively. It is also the same after coating.

Besides the dyeing ability, the protein macromolecular dyes also have filling ability to improve fullness and sponginess of leather. The dyeing and finishing process of the protein macromolecular dyes on leather is convenient under mild reaction conditions.

The protein macromolecular dyes may be used on other protein materials like silk and wool with excellent dyeing result and fastness.

The following examples illustrate the invention. Parts and percentages are by weight unless otherwise stated.

EXAMPLE 1

A mixture of 1000 parts of gelatin, 400 parts of the dye No. 1 in Table 1, 10 parts of $H_3CCOONa$ and 150000 parts of $H_2O$ is stirred in a 1000 ml three-necked flask with a reflux condenser. After the reaction carries out at 85° C. for 2 hours, the pH is adjusted to 7 with 1% $H_3CCOOH$ and the temperature is decreased to make the product become gel. Unreacted parent dyes are washed off. In the obtained protein macromolecular dye, gelatin is the polymeric support matrix, triazinyl is a linking group and the azo dye is the parent dye. The conversion of the parent dye is 95.1%. And the protein macromolecular dye may be in a solution with 10% macromolecule.

EXAMPLES 2~3

A mixture of 1000 parts of casein, 100 parts of the dye No. 2 in Table 1, 15 parts of $ClH_2CCOONa$ and 1000 parts of $H_2O$ is stirred at 70° C. for 10 hours by the method of example 1. In the obtained protein macromolecular dye, casein is the polymeric support matrix and triazinyl is a linking group. The conversion of the parent dye is 95.7%.

The dye No.3 in Table 1 is used to get the protein macromolecular dye and its conversion is 96.1% in accordance with the method of example 2.

EXAMPLES 4~7

A mixture of 1000 parts of casein, 1000 parts of the dye No. 4 in Table 1, 20 parts of $Cl_3CCOONa$ and 50000 parts of $H_2O$ is stirred at 60° C. for 8 hours by the method of example 1. In the obtained protein macromolecular dye, casein is the polymeric support matrix and triazinyl is a linking group.

The dyes No. 5, 6 and 7 in Table 1 are used to get the protein macromolecular dyes in accordance with the method of example 4.

EXAMPLES 8~11

A mixture of 1000 parts of gelatin, 1500 parts of the dye No. 8 in Table 1, 25 parts of $NaB_4O_7 \cdot 10H_2O$ and 100000 parts of $H_2O$ is stirred at 75° C. for 6 hours by the method of example 1. In the obtained protein macromolecular dye, casein is the polymeric support matrix and triazinyl is a linking group.

The dyes No. 9, 10 and 11 in Table 1 are used to get the protein macromolecular dyes in accordance with the example 8.

EXAMPLES 12~15

By the method of example 1, a mixture of 1000 parts of casein, 2000 parts of the dye No. 12 in Table 1, 30 parts of $Na_2CO_3$ and 200000 parts of $H_2O$ is stirred at 80° C. for 5 hours. In the obtained protein macromolecular dye, casein is the polymeric support matrix and triazinyl is a linking group.

The dyes No. 13, 14 and 15 are used to get the protein macromolecular dyes in accordance with the method of example 12.

EXAMPLES 16~19

By the method of example 1, a mixture of 1000 parts of fur-protein, 800 parts of the dye No. 16 in Table 1, 12 parts of $ClH_2CCOONa$ and 120000 parts of $H_2O$ is stirred at 80° C. for 3 hours. In the obtained protein macromolecular dye, fur-protein is the polymeric support matrix and triazinyl is a linking group.

The dyes No. 17, 18 and 19 are used to get the protein macromolecular dyes in accordance with the method of example 16.

EXAMPLES 20~23

By the method of example 1, a mixture of 1000 parts of fur-protein, 1000 parts of the dye No. 20 in Table 1, 20 parts of $NaH_2PO_4$ and 150000 parts of $H_2O$ is stirred at 85° C. for 2 hours. In the obtained protein macromolecular dye, fur-protein is the polymeric support matrix and triazinyl is a linking group.

The dyes No. 21, 22, and 23 in Table 1 are used to get the protein macromolecular dyes in accordance with the method of example 20.

EXAMPLES 24~27

By the method of example 1, a mixture of 1000 parts of gelatin which is modified by methacrylic acid and styrene, 2000 parts of the dye No. 24 in Table 1, 5 parts of $Na_2HPO_4$ and 120000 parts of $H_2O$ is stirred at 85° C. for 1 hour. In the obtained protein macromolecular dye, the modified gelatin is the polymeric support matrix and triazinyl is a linking group.

The dyes No. 25, 26 and 27 in Table 1 are used to get the protein macromolecular dyes in accordance with the method of example 24.

EXAMPLES 28~31

By the method of example 1, a mixture of 1000 parts of casein which is modified by acrylamide and styrene, 300 parts of the dye No. 28 in Table 1, 5 parts of $H_3CCOONa$ and 50000 parts of $H_2O$ is stirred at 75° C. for 4 hours. In the obtained protein macromolecular dye, the modified casein is the polymeric support matrix and triazinyl is a linking group. The conversion of the parent dye is 95.9%.

The dyes No. 29, 30 and 31 are used to get the protein macromolecular dyes and their conversions are 98.4%, 94.6% and 96.7% respectively in accordance with the method of example 28.

EXAMPLES 32~35

A mixture of 1000 parts of fur-protein which is modified by butylacrylate, methyl methacrylate and styrene, 250 parts of the dye No. 32 in Table 1, 5 parts of $Cl_2HCCOONa$ and 100000 parts of $H_2O$ is stirred at 80° C. for 2 hours by the method of example 1. In the obtained protein macromolecular dye, the modified fur-protein is the polymeric support matrix and triazinyl is a linking group. And the conversion of the parent dye is 97.3%.

The dyes No. 33, 34 and 35 are used to get the protein macromolecular dyes and their conversions are 98.2%, 95.4% and 98.9% respectively in accordance with the method of example 32.

EXAMPLE 36

A mixture of 1000 parts of fur-protein, 300 parts of the dye No. 36 in Table 1, 15 parts of $Cl_3CCOONa$ and 150000 parts of $H_2O$ is stirred at 50° C. for 3 hours by the method of example 1. When the reaction is over, the pH is adjusted to 7 with 1% $Cl_3CCOOH$. In the obtained protein macromolecular dye, fur-protein is the polymeric support matrix and triazinyl is a linking group. The conversion of the parent dye is 96.8%. And the protein macromolecular dye may be in a solution with 20% macromolecule.

EXAMPLES 37~49

A mixture of 1000 parts of casein which is modified by caprolactam, 300 parts of the dye No. 37 in Table 1, 15 parts of $NaH_2PO_4$ and 150000 parts of $H_2O$ is stirred at 70° C. by the method of example 1. After the reaction carries out at 45° C. for 2 hours, the protein macromolecular dye is obtained in which modified casein is the polymeric support matrix and triazinyl is a linking group. And the conversion of the parent dye is 95.5%.

The dyes No. 38, 39, 40, 41, 42, 43, 44, 45, 46, 47, 48 and 49 are used to get the protein macromolecular dyes in accordance with the method of example 37. And the conversions of the parent dyes are respectively 95.1%, 96.3%, 97.4%, 95.6%, 94.9%, 98.2%, 96.7%, 97.1%, 95.3%, 96.3%, 97.0% and 96.6%.

EXAMPLE 50

A mixture of 1000 parts of gelatin which is modified by methacrylic acid and styrene, 500 parts of the dye No. 50 in Table 1, 5 parts of $Na_2CO_3$ and 150000 parts of $H_2O$ is stirred in a 1000 ml three-necked flask with a reflux condenser. After the reaction carries out at 30° C. for 5 hours, the pH is adjusted to 7 with 0.5% HCl. In the obtained protein macromolecular dye, the modified gelatin is the polymeric support matrix and pyrimidinyl is a linking group. The conversion of the parent dye is 95.4% and the protein macromolecular dye may be in a solution with 30% macromolecule.

EXAMPLES 51~53

A mixture of 1000 parts of gelatin, 100 parts of the dye No. 51, 52 and 53 respectively in Table 1, 5 parts of $H_3CCOONa$ and 1000 parts of $H_2O$ is stirred at 50° C. for 5 hours by the method of example 50. In the obtained protein macromolecular dye, gelatin is the polymeric support matrix and pyrimidinyl is a linking group.

The dyes No. 52 and 53 are used to get the protein macromolecular dyes in accordance with the method of example 51.

EXAMPLES 54~56

A mixture of 1000 parts of gelatin, 400 parts of the dye No. 54 in Table 1, 10 parts of $ClH_2CCOONa$ and 150000 parts of $H_2O$ is stirred at 65° C. for 2 hours by the method of example 50. In the obtained protein macromolecular dye, gelatin is the polymeric support matrix and pyrimidinyl is a linking group. And the conversion of the parent dye is 97.6%.

The dyes No. 55 and 56 are used to get the protein macromolecular dyes and their conversions are 98.2% and 95.0% respectively in accordance with the method of example 54.

EXAMPLES 57~59

A mixture of 1000 parts of casein, 800 parts of the dye No. 57 in Table 1, 15 parts of $Cl_2HCCOONa$ and 50000 parts of $H_2O$ is stirred at 40° C. for 6 hours by the method of example 50. In the obtained protein macromolecular dye, casein is the polymeric support matrix and pyrimidinyl is a linking group.

The dyes No. 58 and 59 are used to get the protein macromolecular dyes in accordance with the method of example 57.

EXAMPLES 60~62

A mixture of 1000 parts of casein which is modified by methyl methacrylic acid, 1200 parts of the dye No. 60 in Table 1, 20 parts of $Cl_3CCOONa$ and 120000 parts of $H_2O$ is stirred at 55° C. for 5 hours by the method of example 50. In the obtained protein macromolecular dye, the modified casein is the polymeric support matrix and pyrimidinyl is a linking group.

The dyes No. 61 and 62 are used to get the protein macromolecular dyes in accordance with the method of example 60.

EXAMPLES 63~65

A mixture of 1000 parts of fur-protein, 1000 parts of the dye No. 63 in Table 1, 18 parts of $Na_2B_4O_7 \cdot 10H_2O$ and 150000 parts of $H_2O$ is stirred at 70° C. for 2 hours by the method of example 50. In the obtained protein macromolecular dye, fur-protein is the polymeric support matrix and pyrimidinyl is a linking group.

The dyes No. 64 and 65 are used to get the protein macromolecular dyes in accordance with the method of example 63.

EXAMPLES 66~68

A mixture of 1000 parts of fur-protein which is modified by acrylonitrile, methyl methacrylic acid and styrene, 2000 parts of the dye No. 66 in Table 1, 20 parts of $NaHCO_3$ and 200000 parts of $H_2O$ is stirred at 80° C. for 1 hour by the method of example 50. In the obtained protein macromolecular dye, the modified fur-protein is the polymeric support matrix and pyrimidinyl is a linking group.

The dyes No. 67 and 68 are used to get the protein macromolecular dyes in accordance with the method of example 66.

EXAMPLES 69~71

A mixture of 1000 parts of gelatin, 250 parts of the dye No. 69 in Table 1, 5 parts of $Na_2CO_3$ and 60000 parts of $H_2O$ is stirred at 60° C. for 2 hours by the method of example 50. In the obtained protein macromolecular dye, gelatin is the polymeric support matrix and pyrimidinyl is a linking group. The conversion of the parent dye is 98.9%.

The dyes No. 70 and 71 are used to get the protein macromolecular dyes and their conversions are 97.6% and 96.3% respectively in accordance with the method of example 69.

EXAMPLES 72~74

A mixture of 1000 parts of gelatin which is modified by butylacrylate, methyl methacrylic acid and styrene, 800 parts of the dye No. 72 in Table 1, 5 parts of NaOH and 100000 parts of $H_2O$ is stirred at 80° C. for 1 hour by the method of example 50. In the obtained protein macromolecular dyes, the modified gelatin is the polymeric support matrix and pyrimidinyl is a linking group.

The dyes No. 73 and 74 are used to get the protein macromolecular dyes in accordance with the method of example 72.

EXAMPLES 75~77

A mixture of 1000 parts of casein, 400 parts of the dye No. 75 in Table 1, 5 parts of $NaH_2PO_4$ and 80000 parts of $H_2O$ is stirred at 70° C. for 3 hours by the method of example 50. In the obtained protein macromolecular dye, gelatin is the polymeric support matrix and pyrimidinyl is a linking group. The conversion of the parent dye is 98.3%.

The dyes No. 76 and 77 are used to get the protein macromolecular dyes and their conversions are 95.4% and 96.8% respectively in accordance with the method of example 75.

EXAMPLES 78~80

A mixture of 1000 parts of casein which is modified by butylacrylate and methyl methacrylate, 1000 parts of the dye No. 78 in Table 1, 12 parts of $Na_2HPO_4$ and 160000 parts of $H_2O$ is stirred at 50° C. for 4 hours by the method of example 50. In the obtained protein macromolecular dye, the modified gelatin is the polymeric support matrix and pyrimidinyl is a linking group.

The dyes No. 79 and 80 are used to get the protein macromolecular dyes in accordance with the method of example 78.

EXAMPLES 81~83

A mixture of 1000 parts of fur-protein, 300 parts of the dye No. 81 in Table 1, 5 parts of $H_3CCOONa$ and 100000 parts of $H_2O$ is stirred at 70° C. for 4 hours by the method of example 50. In the obtained protein macromolecular dye, fur-protein is the polymeric support matrix and pyrimidinyl is a linking group. The conversion of the parent dye is 95.6%.

The dyes No. 82 and 83 are used to get the protein macromolecular dyes and their conversions are 98.1% and 94.8% respectively in accordance with the method of example 81.

EXAMPLES 84~86

A mixture of 1000 parts of fur-protein which is modified by ethyl acrylate, butyl acrylate and methyl methacrylic acid, 600 parts of the dye No. 84 in Table 1, 10 parts of $ClH_2CCOONa$ and 200000 parts of $H_2O$ is stirred at 60° C. for 3 hours by the method of example 50. In the obtained protein macromolecular dye, fur-protein is the polymeric support matrix and pyrimidinyl is a linking group.

The dyes No. 85 and 86 are used to get the protein macromolecular dyes in accordance with the method of example 84.

EXAMPLES 87~89

A mixture of 1000 parts of gelatin, 500 parts of the dye No. 87 in Table 1, 4 parts of $Na_2HPO_4$ and 150000 parts of $H_2O$ is stirred in a 1000 ml three-necked flask with a reflux condenser. After the reaction carries out at 70° C. for 2 hours, the pH is adjusted to 7 with 0.5% HCl. In the obtained protein macromolecular dye, gelatin is the polymeric support matrix and pyrimidinyl is a linking group. And the conversion of the parent dye is 95.2%. The protein macromolecular dye may be in a solution with 40% macromolecule.

The dyes No. 88 and 89 are used to get the protein macromolecular dye and their conversions are 96.0% and 97.8% respectively in accordance with the method of example 87.

EXAMPLES 90~91

A mixture of 1000 parts of gelatin which is modified by acrylic acid, acrylonitrile and methyl methacrylic acid, 250 parts of the dye No. 90 in Table 1, 2 parts of $Na_2HPO_4$ and 100000 parts of $H_2O$ is stirred at 65° C. for 4 hours by the method of example 87~89. In the obtained protein macromolecular dye, the modified gelatin is the polymeric support matrix and pyrimidinyl is a linking group. The conversion of the parent dye is 95.8%.

The dye No. 91 is used to get the protein macromolecular dye and its conversion is 96.2% in accordance with the method of example 90.

EXAMPLES 92~93

A mixture of 1000 parts of casein, 300 parts of the dye No. 92 in Table 1, 10 parts of $NaHCO_3$ and 150000 parts of $H_2O$ is stirred at 75° C. for 3 hours by the method of example 87~89. In the obtained protein macromolecular dye, casein is the polymeric support matrix and pyrimidinyl is a linking group. The conversion of the parent dye is 95.9% and the protein macromolecular dye may be in a solution with 10% macromolecule.

The dye No. 93 is used to get the protein macromolecular dye and its conversion is 95.3% in accordance with the method of example 92.

EXAMPLES 94~95

A mixture of 1000 parts of casein which is modified by acrylonitrile, butylacrylate and methyl methacrylate, 600 parts of the dye No. 94 in Table 1, 10 parts of $NaHCO_3$ and 200000 parts of $H_2O$ is stirred at 60° C. for 2 hours by the method of example 92~93. In the protein macromolecular dye, the modified casein is the polymeric support matrix and pyrimidinyl is a linking group.

The dye No. 95 is used to get the protein macromolecular dye in accordance with the method of example 94.

EXAMPLE 96

A mixture of 1000 parts of gelatin, 600 parts of the dye No. 96 in Table 2, 10 parts of $Na_2B_4O_7$ 10 $H_2O$ and 150000 parts of $H_2O$ is stirred at 70° C. for 5 hours. When the reaction is over, the temperature is decreased to make the product become gel. Unreacted parent dyes are washed off. In the obtained protein macromolecular dye, gelatin is the polymeric support matrix and ethyl sulfonyl is a linking group. The conversion of the parent dye is 96.3%. The protein macromolecular dye may be in a solution with 10% macromolecule.

EXAMPLES 97~98

A mixture of 1000 parts of fur-protein, 200 parts of the dye No. 97 in Table 2, 5 parts of $CH_3COONa$ and 5000 parts of $H_2O$ is stirred at 70° C. for 3 hours by the method of example 96. In the obtained protein macromolecular dye, fur-protein is the polymeric support matrix and ethyl sulfonyl is a linking group.

The dye No. 98 is used to get the protein macromolecular dye in accordance with the method of example 97.

EXAMPLES 99~101

A mixture of 1000 parts of casein, 800 parts of the dye No. 99 in Table 2, 10 parts of $ClH_2CCOONa$ and 100000 parts of $H_2O$ is stirred at 80° C. for 2 hours by the method of example 96. In the obtained protein macromolecular dye, casein is the polymeric support matrix and ethyl sulfonyl is a linking group.

The dyes No. 100 and 101 are used to get the protein macromolecular dyes in accordance with the method of example 96.

EXAMPLE 102

A mixture of 1000 parts of fur-protein, 300 parts of the dye No. 102 in Table 2, 8 parts of $Cl_2HCCOONa$ and 150000 parts of $H_2O$ is stirred in a 1000 ml three-necked flask with a reflux condenser. After the reaction carries out at 65° C. for 3 hours, the pH is adjusted to 7 with 1% $H_3PO_4$. Unreacted parent dyes are washed off. In the obtained protein macromolecular dye, fur-protein is the polymeric support matrix and ethyl sulfonyl is a linking group. The conversion of the parent dye is 97.8%. The protein macromolecular dye may be in a solution with 20% macromolecule.

EXAMPLES 103~104

A mixture of 1000 parts of fur-protein which is modified by butylacrylate, methyl methacrylate, 300 parts of the dye No. 103 in Table 2, 8 parts of $Cl_3CCOONa$ and 100000 parts of $H_2O$ is stirred at 60° C. for 4 hours by the method of example 102. In the protein obtained macromolecular dye, the modified fur-protein is the polymeric support matrix and ethyl sulfonyl is a linking group. The conversion of the parent dye is 96.5%.

The dye No. 104 is used to get the protein macromolecular dye and its conversion is 95.2% in accordance with the method of example 103.

EXAMPLES 105~106

A mixture of 1000 parts of gelatin, 600 parts of the dye No. 105 in Table 2, 10 parts of $NaH_2PO_4$ and 150000 parts of $H_2O$ is stirred at 70° C. for 3 hours by the method of example 102. In the obtained protein macromolecular dye, gelatin is the polymeric support matrix and ethyl sulfonyl is a linking group. The conversion of the parent dye is 97.2%.

The dye No. 106 is used to get the protein macromolecular dye and its conversion is 97.9% in accordance with the method of example 105.

EXAMPLES 107~108

A mixture of 1000 parts of gelatin which is modified by butylacrylate and methyl methacrylate, 200 parts of the dye No. 107 in Table 2, 5 parts of $Na_2HPO_4$ and 80000 parts of $H_2O$ is stirred at 50° C. for 5 hours by the method of example 102. In the obtained protein macromolecular dye, the modified gelatin is the polymeric support matrix and ethyl sulfonyl is a linking group. The conversion of the parent dye is 95.2%.

The dye No. 108 is used to get the protein macromolecular dye and the conversion of the parent dye is 97.1% in accordance with the method of example 107.

EXAMPLES 109~110

A mixture of 1000 parts of casein, 800 parts of the dye No. 109 in Table 2, 5 parts of $Na_2CO_3$ and 200000 parts of $H_2O$ is stirred at 85° C. for 1 hour by the method of example 102. In the obtained protein macromolecular dye, casein is the polymeric support matrix and ethyl sulfonyl is a linking group.

The dye No. 110 is used to get the protein macromolecular dye in accordance with the method of example 105.

EXAMPLE 111

A mixture of 1000 parts of casein which is modified by acrylonitrile, methyl ethyl acrylate and styrene, 300 parts of the dye No. 111 in Table 2, 2 parts of NaOH and 150000 parts of $H_2O$ is stirred in a 1000 ml three-necked flask with a reflux condenser. After the reaction carries out at 75° C. for 3 hours, the pH is adjusted to 7 with 0.5% HCl. Unreacted parent dyes are washed off. In the obtained protein macromolecular dye, the modified casein is the polymeric support matrix and ethyl sulfonyl is a linking group. The conversion of the parent dye is 97.1%. The protein macromolecular dye may be in a solution with 20% macromolecule.

EXAMPLES 112~113

A mixture of 1000 parts of fur-protein, 600 parts of the dye No. 112 in Table 2, 4 parts of NaOH and 200000 parts of $H_2O$ is stirred at 60° C. for 8 hours by the method of example 111. In the obtained protein macromolecular dye, fur-protein is the polymeric support matrix and ethyl sulfonyl is a linking group. The conversion of the parent dye is 95.2%.

The dye No. 113 is used to get the protein macromolecular dye and its conversion is 97.1% in accordance with the method of example 112.

EXAMPLES 114~116

A mixture of 1000 parts of gelatin which is modified by acrylonitrile, 400 parts of the dye No. 114 in Table 2, 10 parts of $NaH_2PO_4$ and 100000 parts of $H_2O$ is stirred at 70° C. for 4 hours by the method of example 111. In the obtained protein macromolecular dye, the modified gelatin is the polymeric support matrix and ethyl sulfonyl is a linking group. The conversion of the parent dye is 96.3%.

The dyes No. 115 and 116 are used to get the protein macromolecular dyes and their conversions are 95.1% and 95.2% respectively in accordance with the method of example 114.

EXAMPLE 117

Vinylpyridine, vinylpyrrolidone and butylacrylate modify a mixture of casein and gelatin in which their ratio is 7:3. 1000 parts of the modified mixture, 400 parts of the dye No. 117 in Table 2, 4 parts of $Na_2B_4O_7 \cdot 10 H_2O$ and 150000 parts of $H_2O$ are stirred in a 1000 ml three-necked flask with a reflux condenser. After the reaction carries out at 60° C. for 5 hours, the pH is adjusted to 7 with 1% $H_3CCOONa$. Unreacted parent dyes are washed off. In the obtained protein macromolecular dye, the modified mixture of casein and gelatin is the polymeric support matrix and N-ethyl amino sulfonyl is a linking group. The conversion of the parent dye is 95.6%. The protein macromolecular dye may be in a solution with 20% macromolecule.

EXAMPLES 118~120

A 1000 parts mixture of gelatin and casein in which their ratio is 1:1, 200 parts of the dye No. 118 in Table 2, 5 parts of $NaHCO_3$ and 50000 parts of $H_2O$ are stirred at 55° C. for 10 hours by the method of example 117. In the obtained protein macromolecular dye, the mixture of gelatin and casein is the polymeric support matrix and ethyl aminosulfonyl is a linking group. The conversion of the parent dye is 95.3%.

The dyes No. 119 and 120 are used to get the protein macromolecular dyes and the conversion of the parent dye is 96.8% and 95.2% respectively in accordance with the method of example 118.

EXAMPLES 121~123

A mixture of 1000 parts of fur-protein which is modified by vinyl pyridine, vinylpyrrolidone and methyl butylacrylate, 1000 parts of the dye No. 121 in Table 2, 20 parts of $Na_2CO_3$ and 100000 parts of $H_2O$ is stirred at 80° C. for 3 hours by the method of example 117. In the obtained protein macromolecular dye, the modified fur-protein is the polymeric support matrix and N-ethyl aminosulfonyl is a linking group.

The dyes No. 122 and 123 are used to get the protein macromolecular dyes in accordance with the method of example 121.

EXAMPLE 124

A mixture of 1000 parts of casein which is modified by caprolactam, 500 parts of the dye No. 124 in Table 2, 10 parts of $NaH_2PO_4$ and 150000 parts of $H_2O$ are stirred in a 1000 ml three-necked flask with a reflux condenser. After the reaction carries out at 70° C. for 3 hours, the pH is adjusted to 7 with 1% $H_3PO_4$. Unreacted parent dyes is washed off. In the obtained protein macromolecular dye, the modified casein is the polymeric support matrix and N-ethylsulfonyl amino is a linking group. The conversion of the parent dye is 96.2%. And the protein macromolecular dye may be in a solution with 20% macromolecule.

EXAMPLE 125

A mixture of 1000 parts of casein, 150 parts of the dye No. 125 in Table 2, 3 parts of $Na_2HPO_4$ and 5000 parts of $H_2O$ is stirred at 50° C. for 5 hours by the method of example 124. In the obtained protein macromolecular dye, the modified casein is the polymeric support matrix and N-ethyl aminosulfonyl is a linking group. The conversion of the parent dye is 99.0%.

EXAMPLES 126~127

A mixture of 1000 parts of gelatin which is modified by caprolactam, 1000 parts of the dye No. 126 in Table 2, 10 parts of NaOH and 200000 parts of $H_2O$ is stirred at 70° C. for 3 hours by the method of example 124. In the obtained protein macromolecular dye, the modified gelatin is the polymeric support matrix and N-ethyl aminosulfonyl is a linking group.

The dye No. 127 is used to get the protein macromolecular dye in accordance with the method of example 126.

EXAMPLES 128~129

A mixture of 1000 parts of fur-protein, 400 parts of the dye No. 128 in Table 2, 5 parts of $Na_2HPO_4$ and 120000 parts of $H_2O$ is stirred at 40° C. for 8 hours by the method of example 124. In the obtained protein macromolecular dye, the fur-protein is the polymeric support matrix and N-ethyl aminosulfonyl is a linking group.

The dye No. 129 is used to get the protein macromolecular dye in accordance with the method of example 128.

EXAMPLE 130

A mixture of 1000 parts of casein which is modified by acrylonitrile, butylacrylate and styrene, 250 parts of the dye No. 130 in Table 3, 10 parts of $NaHCO_3$ and 150000 parts of $H_2O$ is stirred in a 1000 ml three-necked flask with a reflux condenser. After the reaction carries out at 70° C. for 3 hours, unreacted parent dyes is washed off. In the obtained protein macromolecular dye, the modified casein is the polymeric support matrix and propionamido is a linking group. The conversion of the parent dye is 95.3% and the protein macromolecular dye may be in a solution with 20% macromolecule.

EXAMPLE 131

A mixture of 1000 parts of gelatin which is modified by polyamide, 300 parts of the dye No. 131 in Table 3, 20 parts of $ClCH_2COONa$ and 150000 parts of $H_2O$ is stirred in a 1000 ml three-necked flask with a reflux condenser. After the reaction carries out at 60° C. for 5 hours, the pH is adjusted to 7 with 1% $ClCH_2COOH$. Unreacted parent dyes is washed off. In the obtained protein macromolecular dye, the modified gelatin is the polymeric support matrix and propionamido is a linking group. The conversion of the parent dye is 96.1% and the protein macromolecular dye may be in a solution with 20% macromolecule.

EXAMPLES 132~133

A mixture of 1000 parts of casein which is modified by polyamide, 500 parts of the dye No. 132 in Table 3, 20 parts of $Cl_2CHCOONa$ and 150000 parts of $H_2O$ is stirred at 70° C. for 3 hours by the method of example 131. In the obtained protein macromolecular dye, the modified casein is the polymeric support matrix and propionamido is a linking group. The conversion of the parent dye is 99.3%.

The dye No. 133 is used to get the protein macromolecular dye and its conversion is 95.2% in accordance with the method of example 132.

EXAMPLE 134

A mixture of 1000 parts of gelatin which is modified by butylacrylate, 800 parts of the dye No. 134 in Table 3, 20 parts of $Cl_2HCCOONa$ and 150000 parts of $H_2O$ is stirred in a 1000 ml three-necked flask with a reflux condenser. After the reaction carries out at 75° C. for 4 hours, the protein macromolecular dye is obtained in which the modified gelatin is the polymeric support matrix and chloro propionamido is a linking group.

EXAMPLE 135

A mixture of 1000 parts of gelatin which is modified by methyl methacrylate, 300 parts of the dye No. 135 in Table 3, 20 parts of $Cl_3CCOONa$ and 150000 parts of $H_2O$ is stirred in a 1000 ml three-necked flask with a reflux condenser. After the reaction carries out at 70° C. for 3 hours, the pH is adjusted to 7 with 1% $Cl_3CCOOH$. Unreacted parent dyes is washed off. In the obtained protein macromolecular dye, the modified gelatin is the polymeric support matrix and propionamido is a linking group. The conversion of the parent dye is 96.9% and the protein macromolecular dye may be in a solution with 20% macromolecule.

EXAMPLE 136

A mixture of 1000 parts of casein which is modified by polyamide, 400 parts of the dye No. 136 in Table 3, 20 parts of $H_3CCOONa$ and 100000 parts of $H_2O$ is stirred in a 1000 ml three-necked flask with a reflux condenser. After the reaction carries out at 65° C. for 5 hours, the pH is adjusted to 7 with 1% $H_3CCOOH$. Unreacted parent dyes is washed off. In the obtained protein macromolecular dye, the modified casein is the polymeric support matrix and propionamido is a linking group. The conversion of the parent dye is 96.4% and the protein macromolecular dye may be in a solution with 20% macromolecule.

EXAMPLE 137

A mixture of 1000 parts of fur-protein which is modified by methyl methacrylate, 500 parts of the dye No. 137 in Table 3, 10 parts of $Na_2B_4O_7$ 10 $H_2O$ and 150000 parts of $H_2O$ is stirred in a 1000 ml three-necked flask with a reflux condenser. After the reaction carries out at 80° C. for 1 hour, the pH is adjusted to 7 with 1% $H_3CCOOH$. Unreacted parent dyes is washed off. In the obtained protein macromolecular dye, the modified fur-protein is the polymeric support matrix and propionamido is a linking group. The conversion of the parent dye is 95.9% and the protein macromolecular dye may be in a solution with 20% macromolecule.

EXAMPLES 138~139

A mixture of 1000 parts of fur-protein which is modified by methyl methacrylate, 200 parts of the dye No. 138 in Table 3, 20 parts of $NaHCO_3$ and 150000 parts of $H_2O$ is stirred at 65° C. for 3 hours. In the obtained protein macromolecular dye, the modified fur-protein is the polymeric support matrix and propionamido is a linking group. The conversion of the parent dye is 97.3%.

The dye No. 139 is used to get the protein macromolecular dye and its conversion is 98.0% in accordance with the method of example 138.

EXAMPLE 140

A mixture of 1000 parts of casein which is modified by methyl methacrylate, 100 parts of the dye No. 134 in Table 3, 5 parts of $Na_2CO_3$ and 60000 parts of $H_2O$ is stirred in a 1000 ml three-necked flask with a reflux condenser. After the reaction carries out at 75° C. for 2 hours, the pH is adjusted to 7 with 0.5% HCl. Unreacted parent dyes is washed off. In the obtained protein macromolecular dye, the modified casein is the polymeric support matrix and propionamido is a linking group. The conversion of the parent dye is 98.2% and the protein macromolecular dye may be in a solution with 20% macromolecule.

EXAMPLE 141

A mixture of 1000 parts of casein which is modified by methyl butylacrylate, 700 parts of the dye No. 141 in Table 3, 20 parts of $NaH_2PO_4$ and 150000 parts of $H_2O$ is stirred at 70° C. for 3 hours. In the obtained protein macromolecular dye, the modified casein is the polymeric support matrix and propionamido is a linking group.

The following examples illustrate the application of the protein macromolecular dyes on dyeing leather.

EXAMPLE 142

The 1000 g retanned and neutralized goatskin, the 100 g protein macromolecular dyes synthesized in example 137, 2 g rare earth dyeing assistant and 2000 ml $H_2O$ are rotated at 60° C. in a dyeing drum for 1 hour. Then, another 2 g rare earth dyeing assistant is added. After the drum is continuous turned for 10 another minutes, 80 g amphoteric fatliquoring agent and 40 g sulphated castor oil are added to it. The temperature is kept at 60° C. for 1 hour. 5 g of 36% formaldehyde is added in at 60° C. and the drum is kept to rotate for another 20 minutes. Then 8 g of 88% formic acid is needed to adjust pH and the rotary is continued at 60° C. for 30 minutes. After the dyeing is over, the dyed leather is washed by water and hang drying. The pH of the residual liquid is 4.2~4.5. The fixation of the protein macromolecular dyes is 98.1% on the dyed leather. The dry fastness of the dyed leather is 5 grade and the wet fastness is 4~5 grade.

EXAMPLE 143

The protein macromolecular dye made up in the example 110 is used to dyeing leather by the method of example 142. The fixation of the protein macromolecular dye is 99.3% on the dyed leather, the dry fastness is 5 grade and the wet fastness is 4~5 grade.

EXAMPLE 144

The protein macromolecular dye made up in the example 131 is used to dyeing leather by the method of example 142. The fixation of the protein macromolecular dye is 98.7% on the dyed leather, the dry fastness is 5 grade and the wet fastness is 4~5 grade.

EXAMPLE 145

The dyed leather in example 142 is spray-coated by a base-coat paste of 80 g protein macromolecular dye made up in example 37, 20 g of 20% casein solution, 120 g soft acrylic resin 2# and 400 g $H_2O$. Then the leather is spray-coated by a middle-coat paste of 80 g of the same protein macromolecular dye, 60 g of 10% soft acrylic resin 1#, middling soft acrylic resin 1# and 400 g $H_2O$. The leather is also spray-coated by a top-coat paste of 50 g of 10% formaldehyde, 50 g of 25% middling soft acrylic resin 1#, 100 g of 10% casein solution and 50 g $H_2O$. The last, it is spray-coated by 10% formaldehyde solution. After dried, the spray-coated leather restores soft. The dry fastness is 5 grade and the wet fastness is 4~5 grade.

EXAMPLE 146

By the method of example 145, the macromolecular dye made in example 110 is used to finish dyed leather in example 143. The dry and wet fastness are 5 and 4~5 grade respectively.

EXAMPLE 147

By the method of example 145, the macromolecular dye made up in example 131 is used to finish dyed leather in example 144. The dry fastness is 5 grade and the wet fastness is 4~5 grade.

The following contrast examples illustrate the application of the conventional dyes on dyeing leather.

CONTRAST EXAMPLE 1

By the method of example 142, the direct green dye BE is used to dyeing leather. The dry and wet fastness are 4 and 3 grade respectively.

CONTRAST EXAMPLE 2

By the method of example 142, the acid black dye ATT is used to dyeing leather. The fixation is 83.2%. The dry fastness is 3~4 grade and the wet fastness is 3 grade.

CONTRAST EXAMPLE 3

A base-coat paste of 100 g black pigment paste, 50 g of 10% casein solution, 150 g soft acrylic resin $2^\#$ and 100 g $H_2O$ is used to spray-coat the leather dyed in contrast example 2. A middle-coat paste of 100 g of the same paste, 80 g of 10% casein solution, 110 g soft acrylic resin $1^\#$ and 110 g middling soft acrylic resin $1^\#$ is again spray-coated to the leather. A top-coat paste and formaldehyde spray-coating are the same as the example 145. After it is dried, the spray-coated leather is recovered soft. The dry fastness is 4 grade and the wet fastness is 3 grade.

TABLE 1

| No. | Dye Structural Formula |
|---|---|
| 1 |  |
| 2 |  |
| 3 |  |
| 4 |  |
| 5 |  |

TABLE 1-continued

| No. | Dye Structural Formula |
|---|---|
| 6 | |
| 7 | |
| 8 | |
| 9 | |
| 10 | |
| 11 | |
| 12 | |

TABLE 1-continued

| No. | Dye Structural Formula |
|---|---|
| 13 | |
| 14 | |
| 15 | |
| 16 | |
| 17 | |
| 18 | |
| 19 | |

TABLE 1-continued
| No. | Dye Structural Formula |
|---|---|
| 20 | 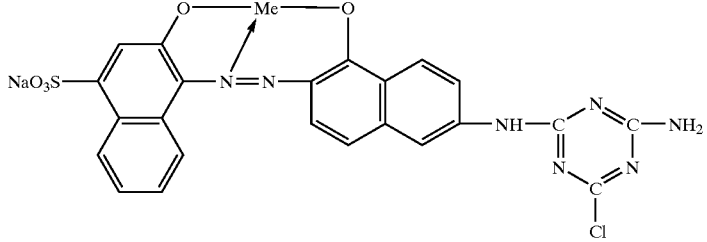
Me = Cr + Co, Cr:Co = 2:1 |
| 21 | 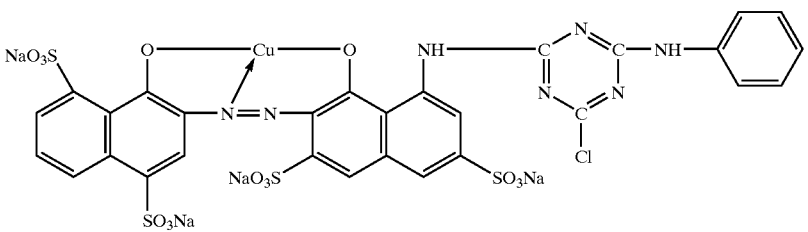 |
| 22 | 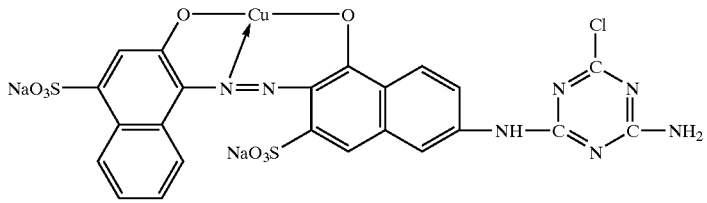 |
| 23 | 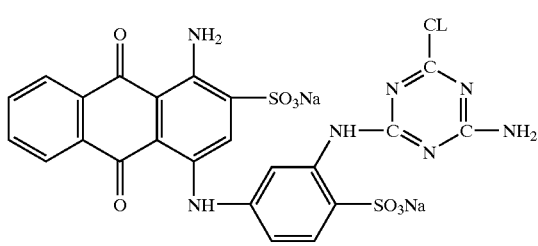 |
| 24 | 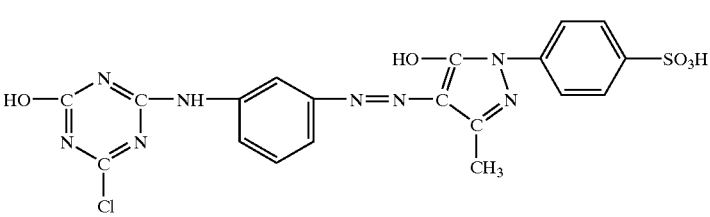 |
| 25 | 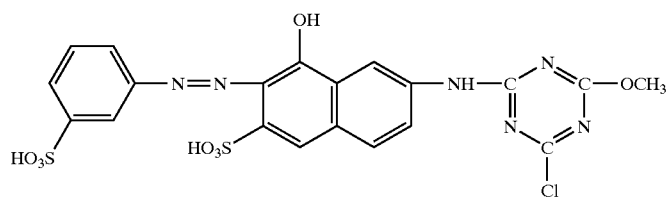 |
| 26 | 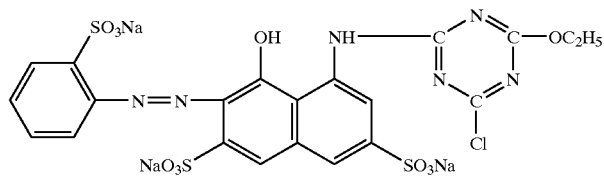 |

TABLE 1-continued
| No. | Dye Structural Formula |
|---|---|
| 27 | 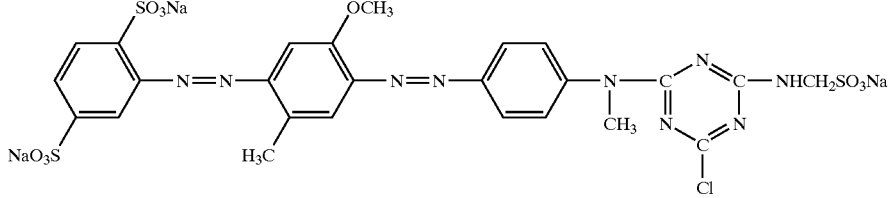 |
| 28 | 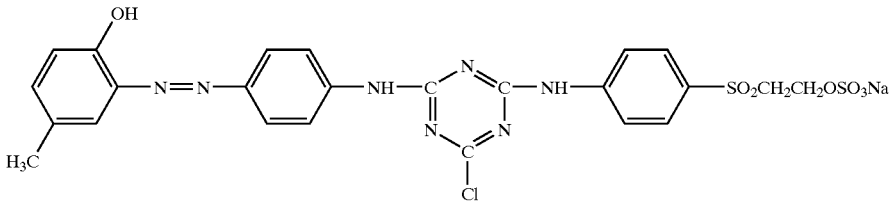 |
| 29 | 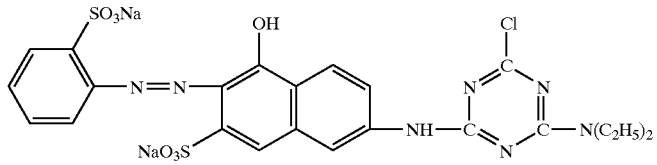 |
| 30 | 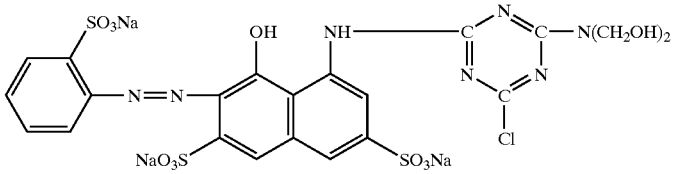 |
| 31 | 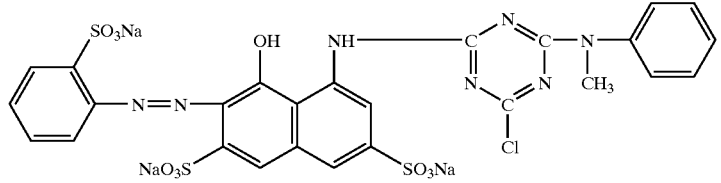 |
| 32 | 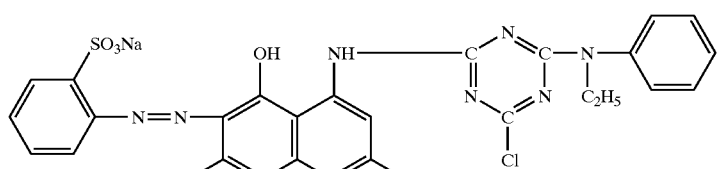 |
| 33 | 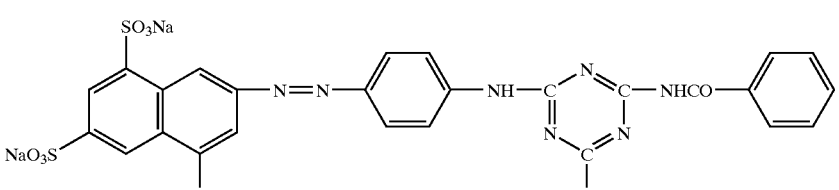 |

TABLE 1-continued
| No. | Dye Structural Formula |
|---|---|
| 34 | 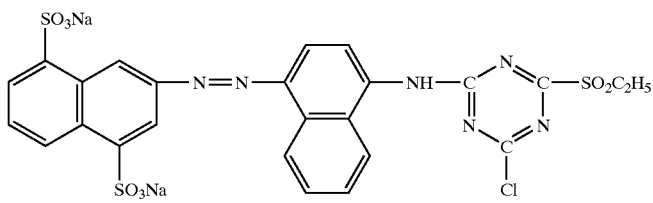 |
| 35 | 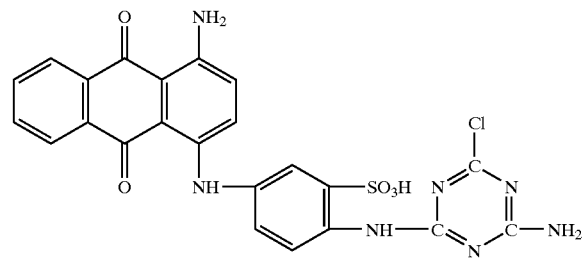 |
| 36 | 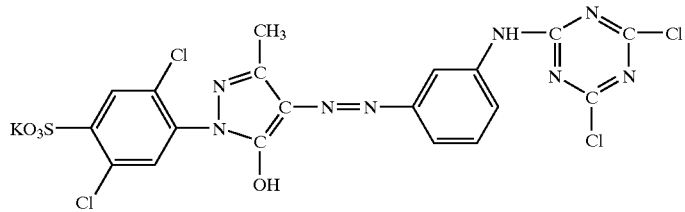 |
| 37 | 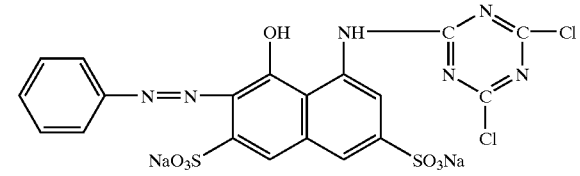 |
| 38 | 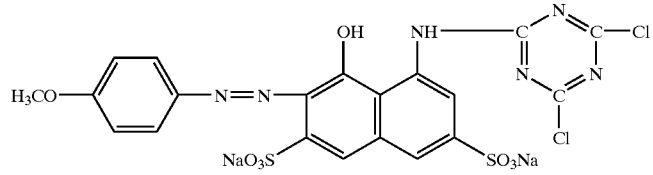 |
| 39 | 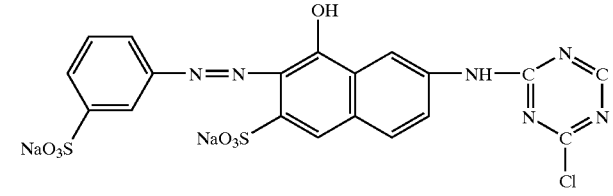 |
| 40 | 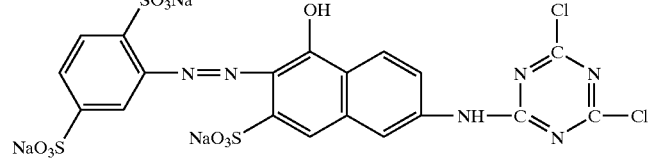 |

TABLE 1-continued

| No. | Dye Structural Formula |
|---|---|
| 41 | |
| 42 | |
| 43 | |
| 44 | |
| 45 | |
| 46 | |

TABLE 1-continued
| No. | Dye Structural Formula |
|---|---|
| 47 | 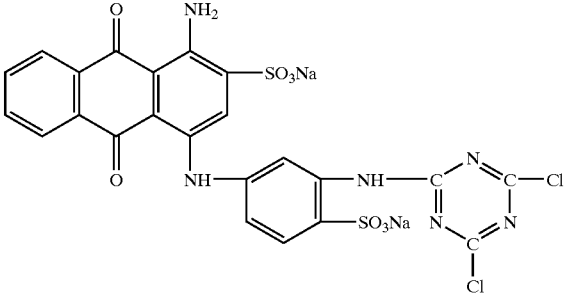 |
| 48 | 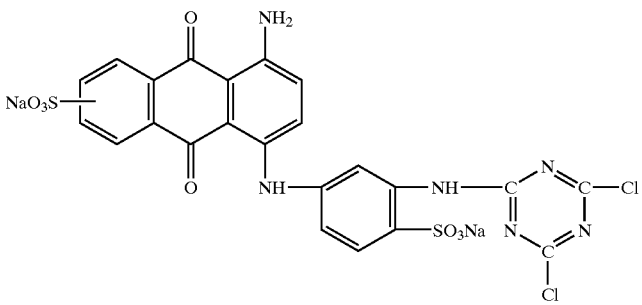 |
| 49 | 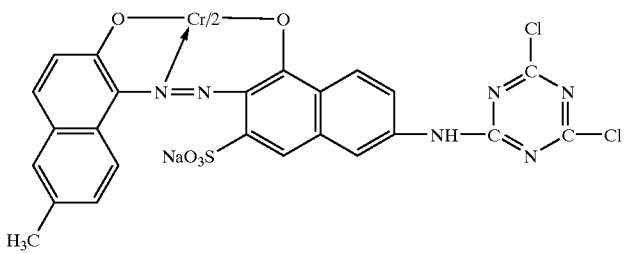 |
| 50 | 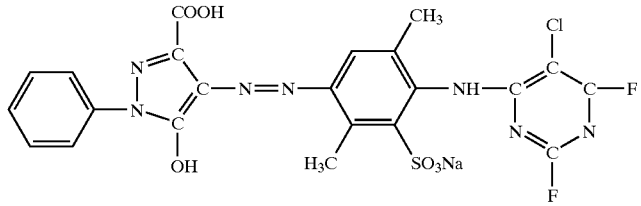 |
| 51 | 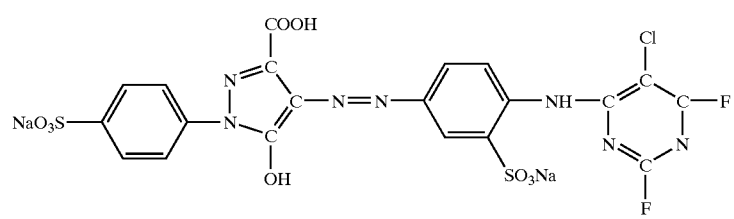 |
| 52 | 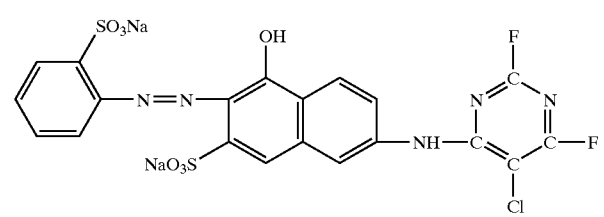 |

TABLE 1-continued

| No. | Dye Structural Formula |
|---|---|
| 53 | |
| 54 | |
| 55 | |
| 56 | |
| 57 | |
| 58 | |
| 59 | |

TABLE 1-continued
| No. | Dye Structural Formula |
|---|---|
| 60 | 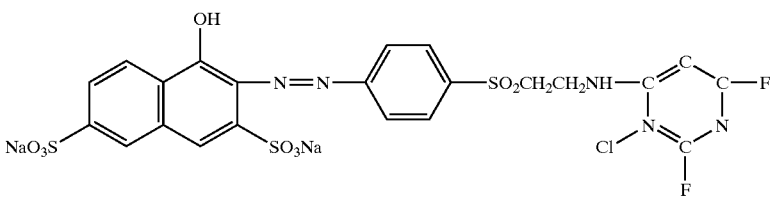 |
| 61 | 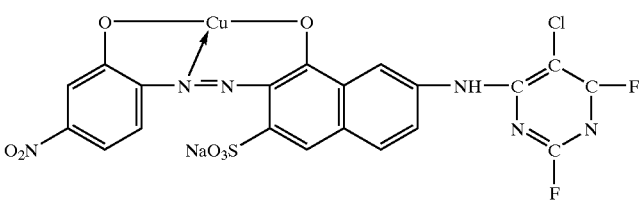 |
| 62 | 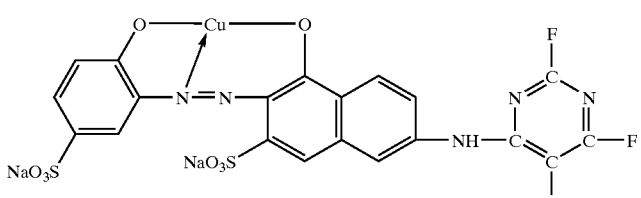 |
| 63 | 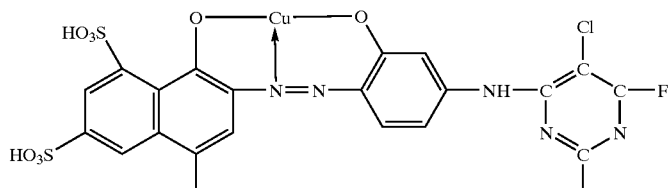 |
| 64 | 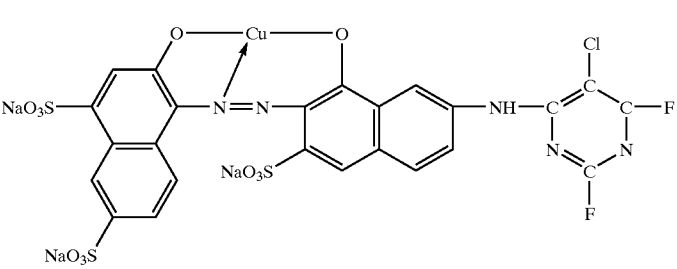 |
| 65 | 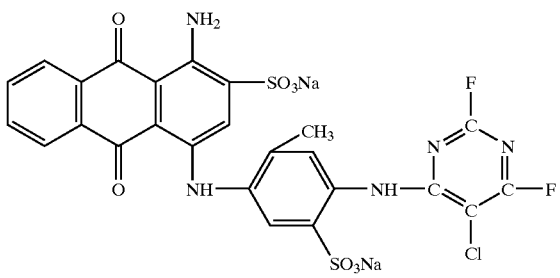 |

TABLE 1-continued

| No. | Dye Structural Formula |
|---|---|
| 66 | |
| 67 | |
| 68 | |
| 69 | |
| 70 | |
| 71 | |

TABLE 1-continued

| No. | Dye Structural Formula |
|---|---|
| 72 | |
| 73 | |
| 74 | |
| 75 | |
| 76 | |
| 77 | |

TABLE 1-continued
| No. | Dye Structural Formula |
|---|---|
| 78 | 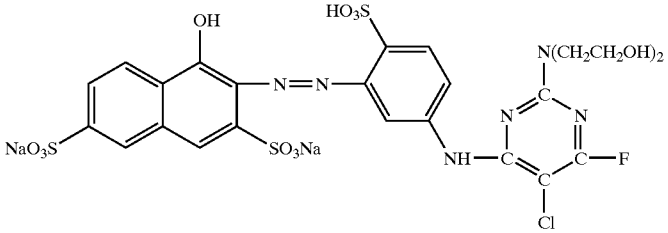 |
| 79 | 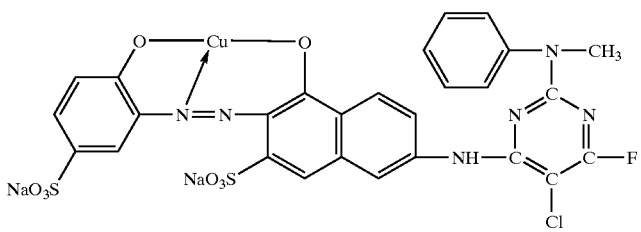 |
| 80 | 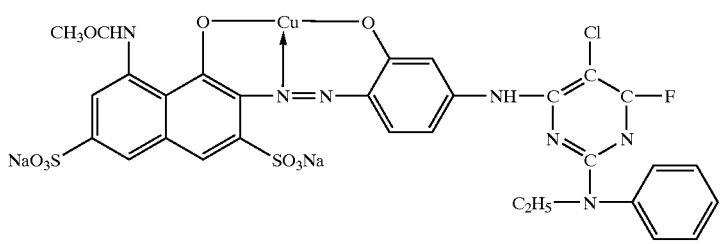 |
| 81 | 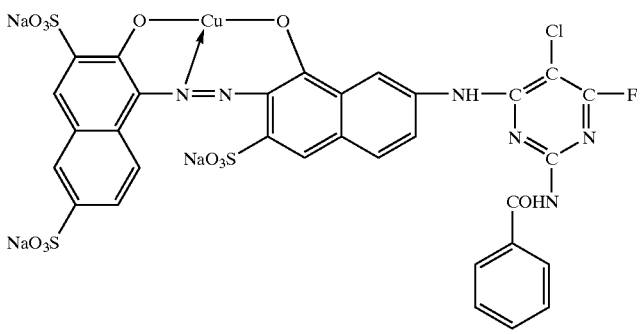 |
| 82 | 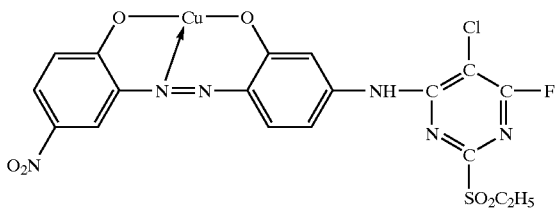 |
| 83 | 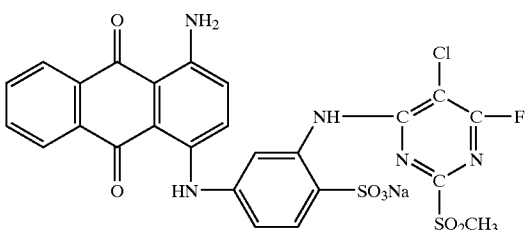 |

TABLE 1-continued

| No. | Dye Structural Formula |
|---|---|
| 84 | |
| 85 | |
| 86 | |
| 87 | |
| 88 | |
| 89 | |

TABLE 1-continued

| No. | Dye Structural Formula |
|---|---|
| 90 | |
| 91 | |
| 92 | |
| 93 | |
| 94 | |
| 95 | |

TABLE 2

| No. | Dye Structure Formula |
|---|---|
| 96 | (structure) |
| 97 | (structure) |
| 98 | (structure) |
| 99 | (structure) |
| 100 | (structure) |
| 101 | (structure) |
| 102 | (structure) |
| 103 | (structure) |

TABLE 2-continued

| No. | Dye Structure Formula |
|---|---|
| 104 | (structure) |
| 105 | (structure) |
| 106 | (structure) |
| 107 | (structure) |
| 108 | (structure) |
| 109 | (structure) |
| 110 | (structure) |

TABLE 2-continued
| No. | Dye Structure Formula |
|---|---|
| 111 | 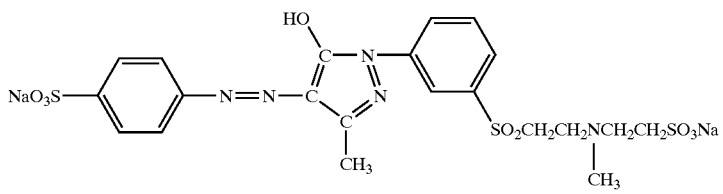 |
| 112 | 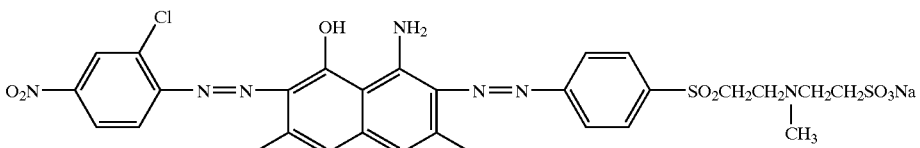 |
| 113 | 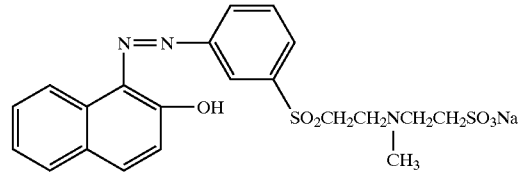 |
| 114 | 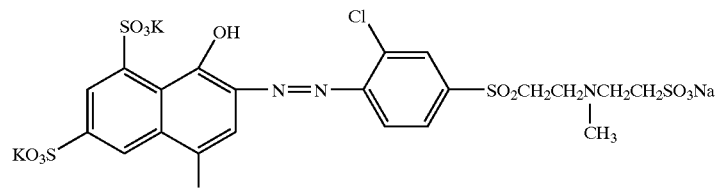 |
| 115 | 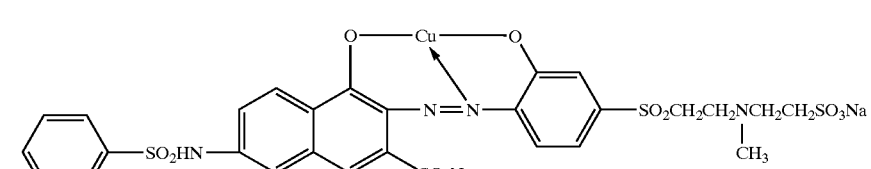 |
| 116 | 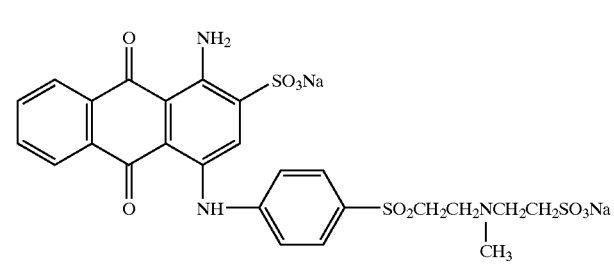 |
| 117 | 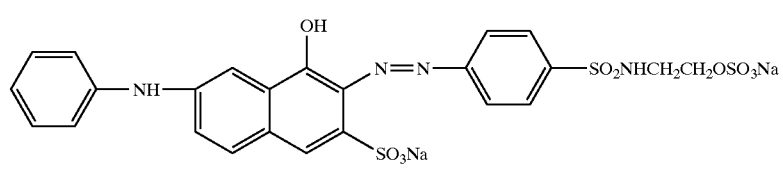 |
| 118 | 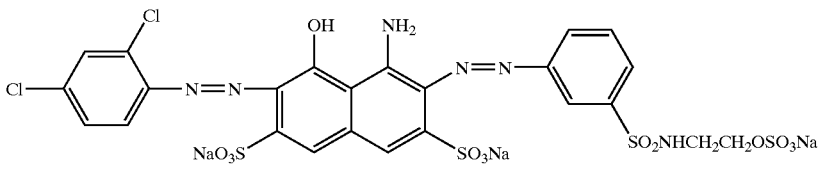 |

TABLE 2-continued
| No. | Dye Structure Formula |
|---|---|
| 119 | 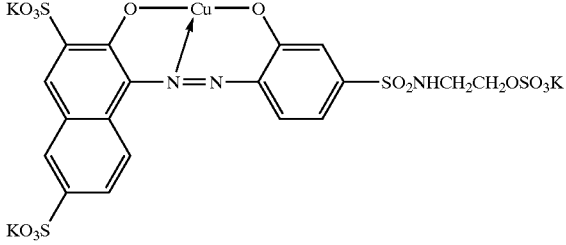 |
| 120 | 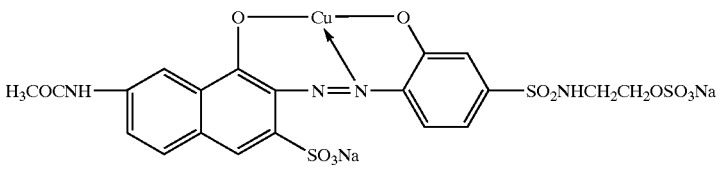 |
| 121 | 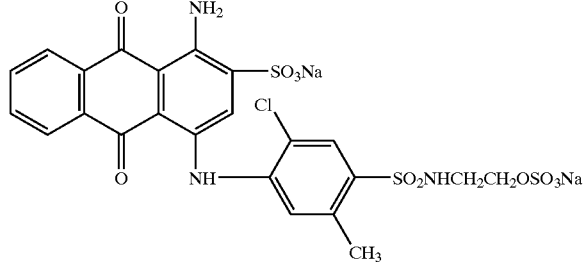 |
| 122 | 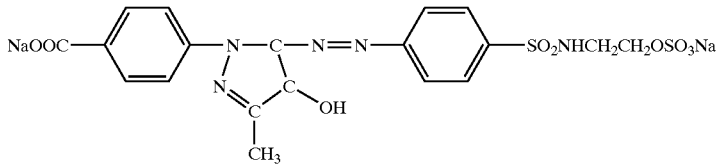 |
| 123 | 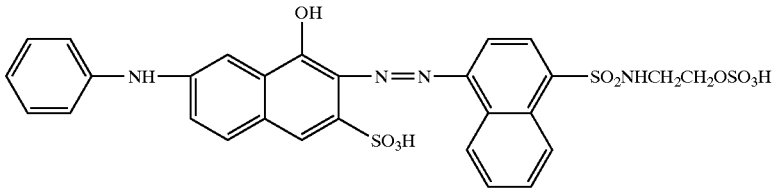 |
| 124 | 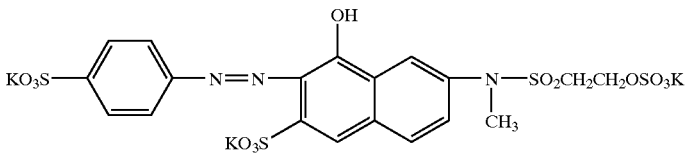 |
| 125 | 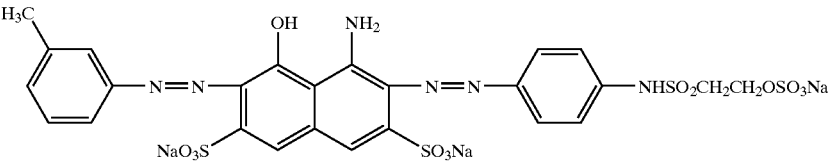 |

TABLE 2-continued

| No. | Dye Structure Formula |
|---|---|
| 126 | (structure: 1-phenylamino-4-[(3-NHSO₂CH₂CH₂OSO₃H)phenylazo]naphthalene-5-sulfonic acid, with HO₃S group) |
| 127 | (Cu-complex azo dye structure with NaO₃S groups, NH-phenyl-N(CH₃)-SO₂CH₂CH₂OSO₃H substituent, SO₃Na groups) |
| 128 | (Cu-complex azo dye structure with NaO₃S groups, N(CH₃)-SO₂CH₂CH₂OSO₃Na substituent) |
| 129 | (anthraquinone structure with NH₂, SO₃Na, and NH-phenyl-N(CH₃)-SO₂CH₂CH₂OSO₃Na substituents) |

TABLE 3

| No. | Dye Structure Formula |
|---|---|
| 130 | (Cr/2 complex azo dye with Cl, NaO₃S, and NHCOCH=CH₂ substituents) |
| 131 | (azo dye with NH₂, HO₃S, and NHCOCBr=CH₂ substituents) |

TABLE 3-continued

| No. | Dye Structure Formula |
|---|---|
| 132 | |
| 133 | |
| 134 | |
| 135 | |
| 136 | |
| 137 | |

TABLE 3-continued

| No. | Dye Structure Formula |
|---|---|
| 138 | |
| 139 | |
| 140 | |
| 141 | |

We claim:

1. A protein macromolecular dye obtained from the chemical reaction of protein macromolecules having amino groups reacted with dye molecules having a reactive group which can react with said amino groups in the protein macromolecule in a form of homogeneous solution, wherein the content of the dye molecules on the protein macromolecule is more than 20% by weight, and wherein the fixation of the protein macromolecular dye when dyeing leather is more than 95%.

2. The protein macromolecular dye of claim 1, wherein said protein macromolecule is selected from the group consisting of casein, gelatin, fur-protein and derivatives thereof.

3. The protein macromolecular dye of claim 1, wherein said protein molecule is a modified protein having one or more moieties selected from the group consisting of

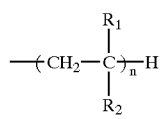  (1)

wherein $R_1$ is —H or —CH$_3$; n is an integer from 1 to 1000;
$R_2$ is —COOH, —CONH$_2$, —CN, —Cl, —COOCH$_3$, —COOC$_2$H$_5$, —COOC$_3$H$_7$, —COOC$_4$H$_9$, —CHO, —COOC$_2$H$_4$OH, or

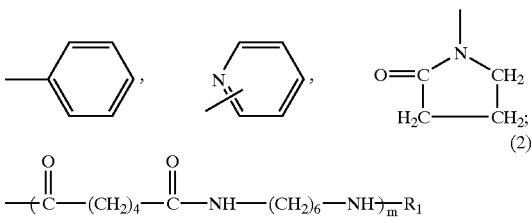  (2)

wherein $m$ is an integer from 1 to 200;
$R_1$ is —H, or

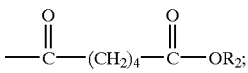

$R_2$ is —H, —CH$_3$, or —C$_2$H$_5$;

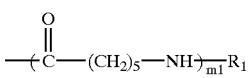  (3)

wherein $m_1$ is an integer from 1 to 300;

$R_1$ is —H, or $$-\overset{O}{\underset{}{C}}-(CH_2)_4-\overset{O}{\underset{}{C}}-OR_2;$$

wherein $R_2$ is —H, —CH$_3$, or —C$_2$H$_5$.

4. The protein macromolecular dye of claim 1, wherein said dye molecules are selected from the group consisting of azo dyes, azo metal complex dyes, and anthraquinone dyes.

5. The protein macromolecular dye of claim 4, wherein said reactive group on the dye molecules is selected from the group consisting of halotriazinyl, halopyrimidinyl, ethylsulfonyl, N-ethyl aminosulfonyl, N-ethyl sulfonylamino, (N-vinylcarbonyl)amino, propioamido, and derivatives thereof.

6. The protein macromolecular dye of claim 4, wherein said azo dye is selected from the group consisting of:

(1)

wherein
- each of $R_1$, $R_4$ and $R_8$ is selected from —H, —Cl, —CH$_3$, —OCH$_3$, —OH, —COOX or —SO$_3$X;
- $R_5$ is —H, —CH$_3$, —COOX, —SO$_3$X, —SO$_2$NH$_2$, or —phenyl;

- each of $R_2$, $R_3$, $R_6$ and $R_7$ represents —H, —Cl, —SO$_3$X, —COOX, —CH$_3$, —NO$_2$, —OCH$_3$, —SO$_2$NHR,

—OSO$_2$—C$_6$H$_4$—R, —OSO$_2$—C$_6$H$_5$, triazinyl with $Y_1$, $Y_2$, R; pyrimidinyl with Q, $Y_1$, $Y_2$, R;

—SO$_2$CH$_2$CH$_2$Y$_3$, —SO$_2$NHCH$_2$CH$_2$Y$_3$,

—N(R)—SO$_2$CH$_2$CH$_2$Y$_3$,

—NHCOCY$_4$=CHY$_5$, and —NHCOCHY$_4$CH$_2$Y$_6$;

wherein
- $Y_1$ is —Cl, —F or —CH$_3$;
- Q is —Cl, —CH$_3$;
- $Y_2$ is —Cl, —F, —R, —OR, —NHCH$_2$SO$_3$X,

—NH—C$_6$H$_4$—SO$_2$CH$_2$CH$_2$OSO$_3$X,

—NHOC—C$_6$H$_5$, —NH—C$_6$H$_4$—SO$_3$X,

—N(R)—C$_6$H$_5$, —NH—C$_6$H$_3$(SO$_3$X)$_2$,

—N(R)$_2$, —N(C$_2$H$_4$OH)$_2$, —N(CH$_2$OH)$_2$, —SO$_2$R;
- $Y_3$ is —Cl, —OSO$_3$X or —N(CH$_3$)CH$_2$CH$_2$SO$_3$X;
- $Y_4$ is —H or —Br;
- $Y_5$ is —H, —Cl or —Br;
- $Y_6$ is —Br or —OSO$_3$X;
- R is —H, —CH$_3$ or —C$_2$H$_5$;
- X is —H, —Na or —K, (2)

wherein
- each of $R_4$, $R_7$ and $R_8$ is selected from —H, —CH$_3$, —OH, —OCH$_3$, —NO$_2$, —SO$_3$X, or —COOX;
- each of $R_1$, $R_2$, $R_3$, $R_5$ and $R_6$ is selected from —H, —Cl, —CH$_3$, —OR, —SO$_3$X, —COOX, —CH$_2$SO$_3$X, —NO$_2$, —N(R)$_2$,

—NH—C$_6$H$_4$—OCH$_3$, —NHCONH$_2$,

—NHCO—C$_6$H$_3$Cl$_2$, —NHCO—C$_6$H$_5$,

—NH—C$_6$H$_5$, —NHO$_2$S—C$_6$H$_4$—R,

—SO$_2$NR—C$_6$H$_5$, —NHCOCH$_3$, triazinyl with $Y_1$, $Y_2$, R; pyrimidinyl with Q, $Y_1$, $Y_2$, R;

—SO₂CH₂CH₂Y₃,

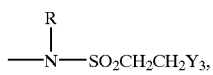

—SO₂NHCH₂CH₂Y₃, —NHCOCY₄=CHY₅, or
—NHCOCHY₄CH₂Y₆;

wherein

Y₁ is —Cl, —F or —CH₃;
Q is —Cl, —CH₃;
Y₂ is —Cl, —F, —R, —OR, —NHCH₂SO₃X,

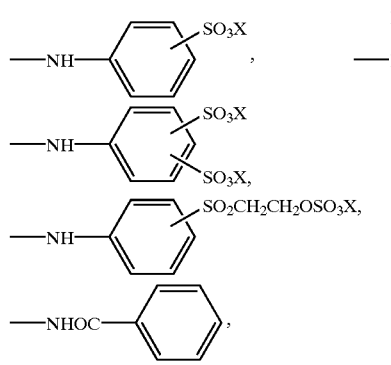

—N(R)₂, —N(CH₂OH)₂, —SO₂R, —N(C₂H₄OH)₂;
Y₃ is —Cl, —OSO₃X or —N(CH₃)CH₂CH₂SO₃X;
Y₄ is —H or —Br;
Y₅ is —H, —Cl or —Br;
Y₆ is —Br or —OSO₃X;
R is —H, —CH₃ or —C₂H₅;
X is —H, —Na or —K, (3)

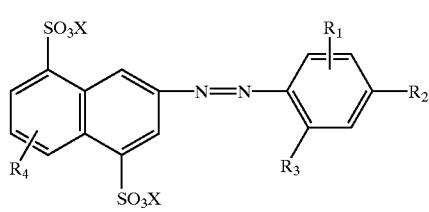

wherein

R₃ is —H, —Cl, —CH₃, —OCH₃, —OH, —COOX, —SO₃X, —SO₂NH₂ or —NHCOCH₃;

each of R₁, R₂ and R₄ is selected from —H, —Cl, —CH₃, —OR, —NO₂, —N(R)₂,

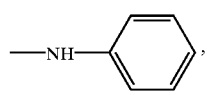

—NHCOCH₃, —NHCONH₂,

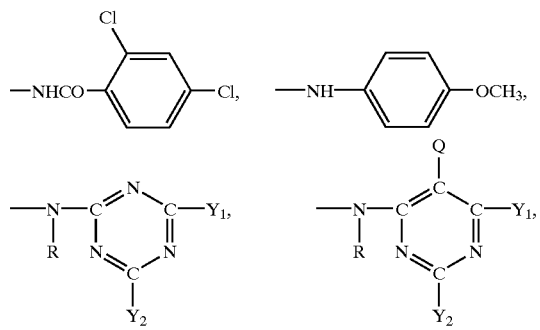

—SO₂CH₂CH₂Y₃, —NHCOCY₄=CHY₅, or

—SO₂NHCH₂CH₂Y₃, —NHCOCHY₄CH₂Y₆;

wherein

Y₁ is —Cl, —F or —CH₃;
Q is —Cl, —CH₃;
Y₂ is —Cl, —F, —R, —OR, —NHCH₂SO₃X,

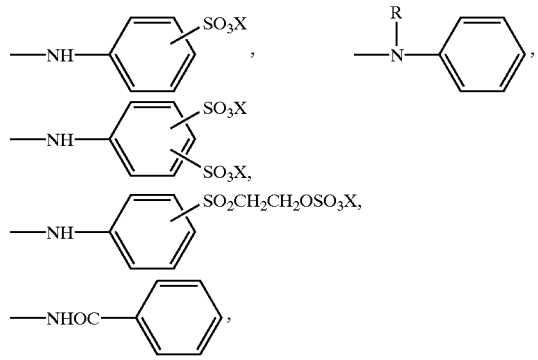

—N(R)₂, —N(CH₂OH)₂, —N(C₂H₄OH)₂, —SO₂R;
Y₃ is —Cl, —OSO₃X or —N(CH₃)CH₂CH₂SO₃X;
Y₄ is —H or —Br;
Y₅ is —H, —Cl or —Br;
Y₆ is —Br or —OSO₃X;
R is —H, —CH₃ or —C₂H₅;
X is —H, —Na or —K.

7. The protein macromolecular dye of claim 4, wherein said azo metal complex dye is selected from the group consisting of:

(1)

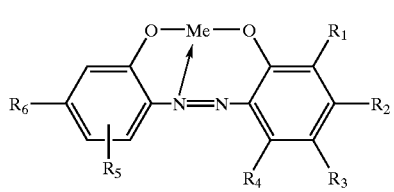

(2)

(3)

(4)

wherein

Me is Cu, Co, Ni or Cr;

each of $R_1$, $R_2$, $R_3$, $R_4$, $R_5$ and $R_6$ is selected from —H, —Cl, —CH$_3$, —OCH$_3$, —SO$_3$X, —COOX, —CH$_2$SO$_3$X, —NH$_2$, —N(CH$_3$)$_2$,

—NH—C$_6$H$_5$, —NH—C$_6$H$_4$—OCH$_3$,

—NHCOCH$_3$, —NHCONH$_2$,

—NHCO—C$_6$H$_5$, —NHCO—C$_6$H$_3$Cl$_2$,

—NHO$_2$S—C$_6$H$_4$—CH$_3$, SO$_2$NH—C$_6$H$_5$, —NO$_2$,

[triazine structure with R, $Y_1$, $Y_2$], [pyrimidine structure with R, Q, $Y_1$, $Y_2$],

—SO$_2$CH$_2$CH$_2$Y$_3$,

—N(R)—SO$_2$CH$_2$CH$_2$Y$_3$

—SO$_2$NHCH$_2$CH$_2$Y$_3$, —NHCOCY$_4$=CHY$_5$, or —NHCOCHY$_4$CH$_2$Y$_6$;

wherein $Y_1$ is —Cl, —F or —CH$_3$;

Q is —Cl, —CH$_3$;

$Y_2$ is —Cl, —F, —R, —OR, —NHCH$_2$SO$_3$X,

—N(R)—C$_6$H$_5$, —NH—C$_6$H$_4$—SO$_3$X,

—NHCH$_2$SO$_3$X, —NH—C$_6$H$_3$(SO$_3$X)$_2$,

—NH—C$_6$H$_4$—SO$_2$CH$_2$CH$_2$OSO$_3$X,

—N(R)$_2$, —N(CH$_2$OH)$_2$, —N(C$_2$H$_4$OH)$_2$, —SO$_2$R,

—NHOC—C$_6$H$_5$;

$Y_3$ is —Cl, —OSO$_3$X or —N(CH$_3$)CH$_2$CH$_2$SO$_3$X;

$Y_4$ is —H or —Br;

$Y_5$ is —H, —Cl or —Br;

$Y_6$ is —Br or —OSO$_3$X;

R is —H, —CH$_3$ or —C$_2$H$_5$;

X is —H, —Na or —K.

8. The protein macromolecular dye of claim 4, wherein said anthraquinone dye is represented by:

[anthraquinone structure with NH$_2$, SO$_3$X, (XO$_3$S)$_m$, NH—(C$_6$H$_{4-n}$)$_n$—G, (J)$_L$]

wherein m or n is 0 or 1 respectively;

L is 0, 1, 2, or 3;

J is —CH$_3$, —Cl, —SO$_3$X; G is

[triazine structure with R, $Y_1$, $Y_2$], [pyrimidine structure with R, Q, $Y_1$, $Y_2$],

—SO$_2$CH$_2$CH$_2$Y$_3$,

—N(R)—SO$_2$CH$_2$CH$_2$Y$_3$,

—SO$_2$NHCH$_2$CH$_2$Y$_3$, —NHCOCY$_4$=CHY$_5$, or —NHCOCHY$_4$CH$_2$Y$_6$;

wherein $Y_1$ is —Cl, —F or —CH$_3$;

Q is —Cl, —CH$_3$;

Y$_2$ is —Cl, —F, —R, —OR, —NHCH$_2$SO$_3$X,

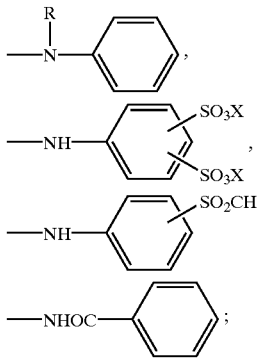

—N(R)$_2$, —N(CH$_2$OH)$_2$, —N(C$_2$H$_4$OH)$_2$, —SO$_2$R,

Y$_3$ is —Cl, —OSO$_3$X or —N(CH$_3$)CH$_2$CH$_2$SO$_3$X;

Y$_4$ is —H or —Br;

Y$_5$ is —H, —Cl or —Br;

Y$_6$ is —Br or —OSO$_3$X;

R is —H, —CH$_3$ or —C$_2$H$_5$;

X is —H, —Na or —K.

9. The protein macromolecular dye of claim 1 wherein the dye and the wet fastness of leather dyed by the protein macromolecular dye are 5 degree and 4 to 5 degree respectively.

10. The protein macromolecular dye of claim 1, wherein the reactive groups of the dyes reacting with the amino groups of the protein macromolecule have the structure:

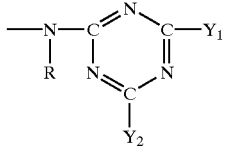
(1)

wherein

Y$_1$ is —Cl, —F or —CH$_3$;

Y$_2$ is —Cl, —F, —R, —OR, —NHCH$_2$SO$_3$X,

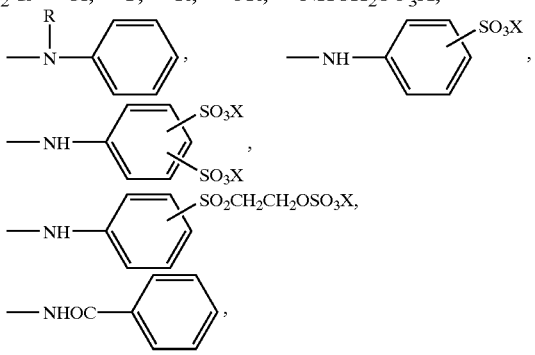

—N(R)$_2$, —N(CH$_2$OH)$_2$, —N(C$_2$H$_4$OH)$_2$, —SO$_2$R;

R is —H, —CH$_3$ or —C$_2$H$_5$;

X is —H, —Na or —K;

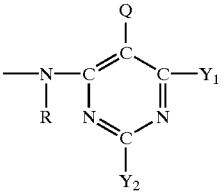
(2)

wherein

Y$_1$ is —Cl, —F or —CH$_3$;

Q is —Cl, or —CH$_3$;

Y$_2$ is —Cl, —F, —R, —OR, —NHCH$_2$SO$_3$X, or

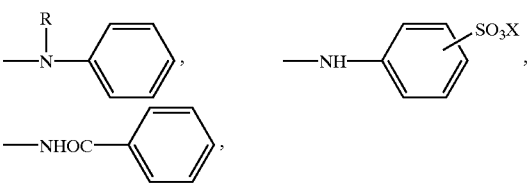

—N(R)$_2$, —N(CH$_2$OH)$_2$, —N(C$_2$H$_4$OH)$_2$, —SO$_2$R,

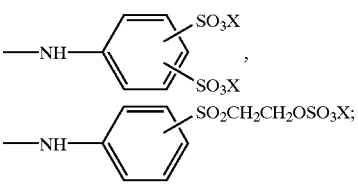

R is —H, —CH$_3$ or —C$_2$H$_5$;

X is —H, —Na or —K;

—SO$_2$CH$_2$CH$_2$Y$_3$ (3)

wherein

Y$_3$ is —Cl, —OSO$_3$X, or —N(CH$_3$)CH$_2$CH$_2$SO$_3$X;

X is —H, —Na, or —K;

—SO$_2$NHCH$_2$CH$_2$Y$_3$ (4)

wherein

Y$_3$ is —Cl, —OSO$_3$X, or —N(CH$_3$)CH$_2$CH$_2$SO$_3$X;

X is —H, —Na, or —K;

—NR—SO$_2$CH$_2$CH$_2$Y$_3$ (5)

wherein

Y$_3$ is —Cl, —OSO$_3$X, or —N(CH$_3$)CH$_2$CH$_2$SO$_3$X;

R is —H, —CH$_3$, or —C$_2$H$_5$;

X is —H, —Na, or —K;

—NHCOCY$_4$=CHY$_5$ (6)

wherein

Y$_4$ is —H, or —Br;

Y$_5$ is —H, —Cl, or —Br;

—NHCOCHY$_4$CH$_2$Y$_6$ (7)

wherein

Y$_4$ is —H, or —Br;

Y$_6$ is —Br, or —OSO$_3$X;

X is —H, —Na, or —K.

* * * * *

UNITED STATES PATENT AND TRADEMARK OFFICE
CERTIFICATE OF CORRECTION

PATENT NO.     : 6,689,870 B1
DATED          : February 10, 2004
INVENTOR(S)    : Yang et al.

It is certified that error appears in the above-identified patent and that said Letters Patent is hereby corrected as shown below:

Title page,
Insert Item -- [30]     Foreign Application Pirority Data
            July 16, 1997 (CN)     97112231.8 --.

Columns 49-50,
Number 19, the formula should read:

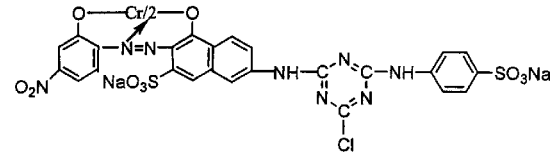

Columns 53-54,
Number 32, the formula should read:

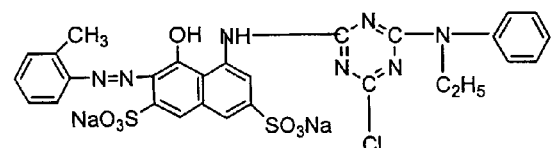

Columsn 59-60,
Number 51, the formula should read:

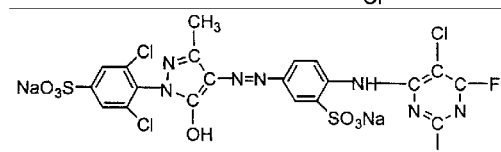

Columns 61-62,
Number 58, the formula should read:

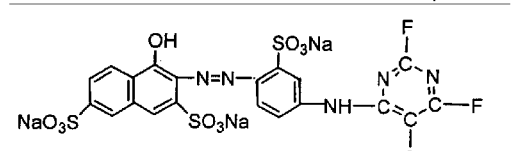

Columns 71-72,
Number 84, the formula should read:

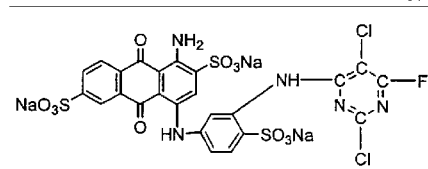

Number 85, the formula should read:

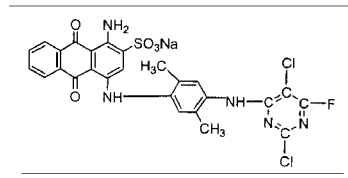

Columns 75-76,
Number 100, the formula should read:

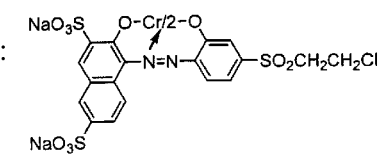

UNITED STATES PATENT AND TRADEMARK OFFICE
CERTIFICATE OF CORRECTION

PATENT NO. : 6,689,870 B1
DATED : February 10, 2004
INVENTOR(S) : Yang et al.

It is certified that error appears in the above-identified patent and that said Letters Patent is hereby corrected as shown below:

Column 95,
Line 34, "dye of claim 1" should read -- dye of claim 5 --.

Signed and Sealed this

Thirteenth Day of July, 2004

JON W. DUDAS
*Acting Director of the United States Patent and Trademark Office*